US012138433B2

(12) United States Patent
Mayle, Jr. et al.

(10) Patent No.: US 12,138,433 B2
(45) Date of Patent: Nov. 12, 2024

(54) ASPIRATION AND INJECTION DEVICES

(71) Applicant: VELOJECT, LLC, San Francisco, CA (US)

(72) Inventors: Robert E. Mayle, Jr., Kentfield, CA (US); Erik J. Shahoian, Sonoma, CA (US); Terrence C. Smith, Portland, OR (US)

(73) Assignee: Veloject, LLC, San Francisco, CA (US)

( * ) Notice: Subject to any disclaimer, the term of this patent is extended or adjusted under 35 U.S.C. 154(b) by 0 days.

(21) Appl. No.: 18/552,893

(22) PCT Filed: Oct. 5, 2022

(86) PCT No.: PCT/US2022/077620
§ 371 (c)(1),
(2) Date: Sep. 27, 2023

(87) PCT Pub. No.: WO2023/060135
PCT Pub. Date: Apr. 13, 2023

(65) Prior Publication Data
US 2024/0091457 A1   Mar. 21, 2024

Related U.S. Application Data

(60) Provisional application No. 63/322,645, filed on Mar. 23, 2022, provisional application No. 63/252,607, filed on Oct. 5, 2021.

(51) Int. Cl.
*A61M 5/315* (2006.01)
*A61M 39/24* (2006.01)

(52) U.S. Cl.
CPC ........ *A61M 5/31581* (2013.01); *A61M 39/24* (2013.01); *A61M 2205/36* (2013.01); *A61M 2205/583* (2013.01)

(58) Field of Classification Search
CPC ........... A61M 1/00; A61M 1/60; A61M 1/71; A61M 1/734; A61M 1/74; A61M 1/7413;
(Continued)

(56) References Cited

U.S. PATENT DOCUMENTS 3,597,113 A   8/1971   Dumoulin
5,076,769 A   12/1991  Shao
(Continued)

FOREIGN PATENT DOCUMENTS

JP   H06142199 A    5/1994
WO   WO88/003815 A1   6/1988
(Continued)

*Primary Examiner* — Kevin C Sirmons
*Assistant Examiner* — Alexandra Lalonde
(74) *Attorney, Agent, or Firm* — Shay Glenn LLP

(57) ABSTRACT

Apparatuses and methods for continuous injection of fluid, in some examples the apparatuses may include a manifold, a pair of reciprocating pistons, and an actuation control that may apply both suction (aspiration) and injection of fluid as part of the same actuation. The apparatuses and methods may be configured to simplify operation of a continuous fluid injection apparatus, including operations that include an aspiration an injection of fluid to confirm the absence/presence of blood prior to injection.

8 Claims, 23 Drawing Sheets

(58) Field of Classification Search
CPC .......... A61M 1/743; A61M 1/76; A61M 1/77;
A61M 1/772; A61M 1/774; A61M 1/777;
A61M 1/782; A61M 1/80; A61M 1/81;
A61M 1/815; A61M 1/87; A61M 5/00;
A61M 5/1407; A61M 5/1408; A61M
5/142; A61M 5/14212; A61M 5/14216;
A61M 5/1422; A61M 5/14228; A61M
5/145; A61M 5/1452; A61M 5/14526;
A61M 5/168; A61M 5/16804; A61M
5/16813; A61M 5/16827; A61M 5/16877;
A61M 5/16881; A61M 5/178; A61M
5/1782; A61M 5/19; A61M 5/20; A61M
5/2066; A61M 5/2448; A61M 5/284;
A61M 5/31; A61M 5/315; A61M
5/31511; A61M 5/31565; A61M 5/31576;
A61M 5/31578; A61M 5/3158; A61M
5/31581; A61M 5/31585; A61M 5/3159;
A61M 5/31596; A61M 5/3294; A61M
5/445; A61M 2005/14208; A61M
2005/14513; A61M 2005/1787; A61M
2005/3128; A61M 2005/31598; A61M
39/22; A61M 39/24; A61M 39/223;
A61M 2039/224; A61M 2039/242; A61M
2039/2433; A61M 2039/2473; A61M
2039/2486; A61M 2039/2493; A61M
2039/0027; A61M 2205/127; A61M
2205/128; A61M 2205/33; A61M
2205/331; A61M 2205/334; A61M
2205/337; A61M 2205/36; A61M
2205/58; A61M 2205/583; A61M
2209/045; A61J 1/20; A61J 1/2048; A61J
1/2058; A61J 1/2062; A61J 1/2089; A61J
1/2093; A61J 1/2096

See application file for complete search history.

(56) References Cited

U.S. PATENT DOCUMENTS

| 5,232,024 | A | 8/1993 | Williams |
| 5,492,535 | A | 2/1996 | Reed et al. |
| 5,755,224 | A | 5/1998 | Good et al. |
| 5,916,197 | A | 6/1999 | Reilly et al. |
| 5,921,951 | A | 7/1999 | Morris |
| 6,022,329 | A | 2/2000 | Arnett et al. |
| 6,428,518 | B1 | 8/2002 | Brengle et al. |
| 7,638,958 | B2 | 12/2009 | Philipp et al. |
| 8,382,703 | B1 | 2/2013 | Abdelaal |
| 9,770,551 | B1 | 9/2017 | Faden |
| 10,463,791 | B2 | 11/2019 | Shergold et al. |
| 11,565,055 | B2 | 1/2023 | Mayle et al. |
| 11,590,292 | B2 | 2/2023 | Mayle et al. |
| 2006/0292304 | A1 | 12/2006 | Tisone |
| 2008/0045925 | A1* | 2/2008 | Stepovich ......... A61M 5/16827 604/82 |
| 2008/0167621 | A1* | 7/2008 | Wagner .................. A61M 5/19 600/432 |
| 2009/0043441 | A1 | 2/2009 | Breed |
| 2010/0160900 | A1 | 6/2010 | Khoun et al. |
| 2010/0286650 | A1 | 11/2010 | Fitzgerald |
| 2011/0002802 | A1 | 1/2011 | Capone et al. |
| 2011/0196309 | A1 | 8/2011 | Wells |
| 2012/0053557 | A1 | 3/2012 | Abal |
| 2012/0244018 | A1 | 9/2012 | Reilly |
| 2012/0265128 | A1 | 10/2012 | Kolin |
| 2013/0053816 | A1 | 2/2013 | Diperna et al. |
| 2013/0150825 | A1 | 6/2013 | Rimsa et al. |
| 2014/0134001 | A1 | 5/2014 | Uchida et al. |
| 2014/0224829 | A1 | 8/2014 | Capone et al. |
| 2015/0029816 | A1 | 1/2015 | Beyer et al. |
| 2015/0032054 | A1 | 1/2015 | Eberhard |
| 2015/0157789 | A1 | 1/2015 | Capone et al. |
| 2015/0174321 | A1 | 6/2015 | Cohen |
| 2015/0182685 | A1 | 7/2015 | Henniges et al. |
| 2015/0320964 | A1 | 11/2015 | Guzman |
| 2015/0343137 | A1 | 12/2015 | Bonnette et al. |
| 2016/0235920 | A1 | 8/2016 | Finke et al. |
| 2016/0263319 | A1 | 9/2016 | Brandelis |
| 2017/0021951 | A1 | 1/2017 | Teague |
| 2017/0119953 | A1 | 5/2017 | Wen |
| 2017/0290987 | A1 | 10/2017 | Mandaroux et al. |
| 2017/0298929 | A1 | 10/2017 | Littich |
| 2018/0043088 | A1 | 2/2018 | Adams et al. |
| 2019/0117921 | A1 | 4/2019 | Bender, II et al. |
| 2019/0201615 | A1 | 7/2019 | You et al. |
| 2019/0247569 | A1 | 8/2019 | Dern et al. |
| 2019/0365993 | A1 | 12/2019 | Staub et al. |
| 2021/0308386 | A1 | 10/2021 | Mayle et al. |
| 2023/0211091 | A1 | 7/2023 | Mayle et al. |

FOREIGN PATENT DOCUMENTS

| WO | WO2014/104338 A1 | 7/2014 |
| WO | WO2018/203203 A1 | 11/2018 |
| WO | WO2019/003220 A1 | 1/2019 |
| WO | WO2021/207122 A1 | 10/2021 |
| WO | WO2023/060135 A1 | 4/2023 |

* cited by examiner

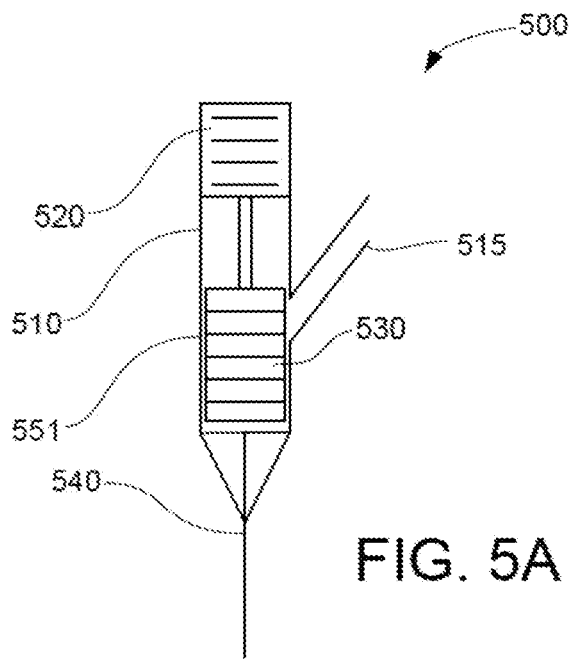
FIG. 5A
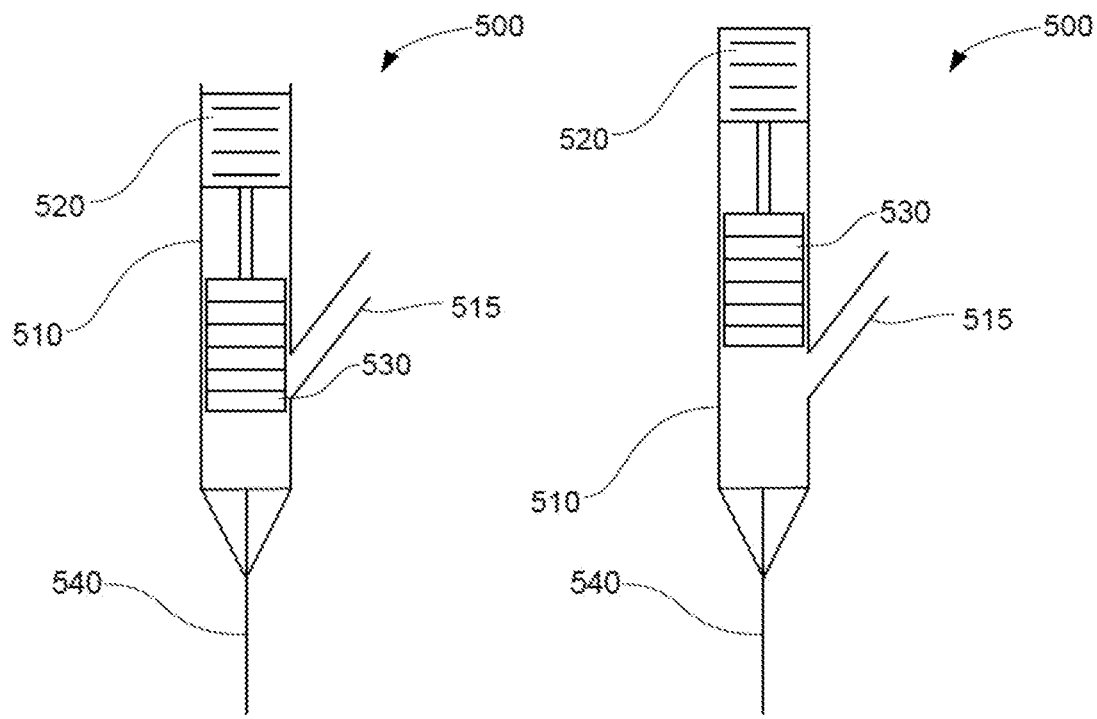
FIG. 5B
FIG. 5C

ASPIRATION AND INJECTION DEVICES

CLAIM OF PRIORITY

This patent application is a U.S. National Phase application under 35 U.S.C. 371 of International Patent Application No. PCT/US2022/077620, titled "ASPIRATION AND INJECTION DEVICES," filed Oct. 5, 2022, now International Patent Application Publication No. WO 2023/060135, which claims priority to U.S. provisional patent application No. 63/252,607, titled "STIMULATION, ASPIRATION, AND INJECTION DEVICES," filed on Oct. 5, 2021, and U.S. provisional patent application No. 63/322,645, titled "STIMULATION, ASPIRATION, AND INJECTION DEVICES," filed on Mar. 23, 2022, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

BACKGROUND

Every year, more than 600,000 knee replacements and more than 300,000 hip replacements are performed in the United States alone. Some 2.6 million people get facial cosmetic surgery. Pain medications for replacements and fillers for cosmetic surgery are delivered into multiple locations on a knee, hip or face, requiring a relatively large number of injections of significant volumes. Tissues in the knee, hip, and face, such as muscle, ligaments, and tendons, and other connective tissue are dense and fibrous and resist injection, at least in part because pain medications for replacements and fillers for cosmetic surgery are viscous. Viscous fluid typically does not flow well. Viscous fluids can be difficult to expel from a syringe (the current method for delivering these fluids. Expelling a viscous fluid or injecting a resistant tissue requires higher pressure; thus viscous solutions generally take more time to inject and injecting large quantities of pain medications and fillers can be time-consuming. Expelling a viscous fluid from a syringe can be hard on the operator's hands, and in particular, expelling a large quantity of fluid from a syringe can be hard on the operator's hands. This difficulty may be compounded when injecting a fluid into resistant tissues.

Current methods of delivering viscous fluids using hand-held syringes suffers from these and other many drawbacks. What is needed are apparatuses and methods to deliver viscous fluids in a manner that may address these drawbacks and delivers pain medications, fillers, and other viscous fluids in a manner that is easy, safe, and fast for the benefit of both the patient and the operator providing the treatment.

In addition, oftentimes prior to an injection of a pharmaceutical, a clinician may verify a treatment region using an ultrasound device or by delivering electrical energy to the region and then monitoring the patient. The electrical energy may provoke a response that verifies the treatment region. Conventionally, after the treatment region is verified, another device is used to deliver a liquid (i.e., a liquid pharmaceutical) to the treatment region. In some cases, the delivery of the pharmaceutical may require a second clinician to aspirate and/or inject the drug. Using multiple devices and/or multiple clinicians to verify location and deliver the pharmaceutical may crowd the working area with clinicians and equipment. Some venues, such as an operating room, may be constrained in the amount of space that is available.

SUMMARY OF THE DISCLOSURE

Described herein are methods and apparatuses (e.g., devices, systems, assemblies, etc.) for injecting fluid, and particularly viscus fluid, into a tissue. These apparatuses may be hand-held apparatuses that can deliver multiple doses of pre-set (e.g., selectable) volumes and/or pressures and/or flow rates of viscus material into the tissue.

In general, these apparatuses (e.g., systems, devices, etc.) and method may be configured to simplify the operation of a continuous fluid injection system, including one that aspirated prior to injection to confirm the absence/presence of blood. These apparatuses may also be configured to be less complicated and easier to operate than other injection systems.

For example, described herein are systems for injecting a fluid, the system comprising: a manifold, wherein the manifold comprises a selection channel and a function selection piston in the selection channel that is configured to move within the selection channel; a plurality of check valves in the manifold; a first piston chamber fluidically connected to the selection channel and in fluid communication with a reservoir port; a second piston chamber fluidically connected to the selection channel in fluid communication with the reservoir port; a delivery port fluidically connected to the selection channel; an actuation control configured to drive the function selection piston within the selection channel so that, at a start of an actuation of the actuation control, the function selection piston causes aspiration into the selection channel from the delivery port, further wherein continuing the actuation of the actuation control moves the function selection piston so that the first piston chamber and the second piston chamber are in fluid communication with the delivery port, so that fluid is pumped out of the delivery port from the first piston chamber and the second piston chamber.

The reservoir port may generally be configured to couple to a removable reservoir. For example, the reservoir port may comprise a luer lock coupler that is configured to couple to a syringe (e.g., a 60 cc syringe, or any appropriately sized syringe, tank, etc.).

Any of these apparatuses and methods may include an aspiration window configured to display aspirated material. In some cases it may be desirable to avoid injecting into a blood vessel, thus aspiration may confirm the location of the needle outside of blood vessel. The aspiration window may be part of an aspiration region. In some cases one or more sensors (e.g., optical sensors) may be used in addition to or instead of a window for detecting aspirate (e.g., for detecting blood in the aspiration region). If a sensor is used, the apparatus may include an output (e.g., visual, such as an LED, audible, such as a tone, etc.) to alert the user that the aspirate does not include blood and/or does include blood. The aspiration region and/or aspiration window may be between the delivery port and the selection channel (e.g., at a distal end region of the apparatus). The aspiration region may be a part of the selection channel.

In any of these systems the actuation control may include a trigger (or button, knob, etc.). The actuation control may allow the user to operate the apparatus, which is generally configured as a hand-held (single-hand) operated device, with the same hand that is gripping or holding the apparatus. For example, the actuation control may be configured as trigger than may be pulled by a finger. In any of these apparatuses the actuation control may be configured so that initial activating of the actuation control (e.g., the first pull on the trigger, push of a button, etc.) may result in movement of the selection piston in the selection channel to a first (aspiration) position, moving the selection piston proximally away from the outlet port (to which a needle may be coupled). This initial movement may draw material into the selection channel (aspiration). Continuing to pull the trigger/push the button (or pulling harder, pushing harder, etc.) may move the selection piston further proximally in the selection channel, reversing the flow of material in the selection channel by exposing the fluid connection to the first and second piston chambers and activating the reciprocating movement of the pistons within the (typically small-volume) first and second piston chambers, so that fluid may be expelled out of the delivery port (and therefore out of the needle). When injection is complete (either because the user release the control (e.g., trigger, button, etc.) or because of a timer or sensed delivered volume has been completed, injection may be stopped by driving the selection piston distally again and stopping the reciprocating movement of the first and second pistons.

Thus, in any of these system the manifold may further comprise a first piston channel in fluid connection with each of: the first piston chamber, the selection channel and the reservoir port; wherein the manifold further comprises a second piston channel in fluid connection with the second piston chamber, the selection channel and the reservoir port. The plurality of check valves may comprise: a first check valve configured to prevent backflow from the selection channel into the first piston channel, a second check valve configured to prevent backflow from the first piston channel to the reservoir port, a third check valve configured to prevent backflow from the selection channel into the second piston channel, and a fourth check valve configured to prevent backflow from the second piston channel to the reservoir port.

As mentioned, the actuation control may be configured to drive the function selection piston proximally from a first position in which the fluid connection between the selection channel and both the first piston chamber and the second piston chamber may be obstructed to a second position in which the fluid connection between the selection channel and both the first piston chamber and the second piston chamber is not obstructed.

As mentioned, the actuation control may be configured so that continuing the actuation triggers a drive assembly to drive reciprocation of a first piston in the first piston chamber and a second piston in the second piston chamber.

Any of the apparatuses described herein may include a drive assembly comprising a transmission operatively connected to a first piston in the first piston chamber and a second piston in the second piston chamber, wherein the drive assembly reciprocally moves the first piston and the second piston to drive fluid out of the delivery port while alternately transferring fluid through the reservoir port into the first piston chamber and the second piston chamber. Any of these apparatuses may include a motor coupled to the drive assembly.

In general, these apparatuses may be configured as a hand-held/hand-operated apparatus that include a first disposable component including the manifold and pistons, and a second (reusable) component including the drive assembly (e.g., motor, controller, power supply, drive belt, etc.), and a single-use or limited-use (e.g., disposable) fluid-handling component that includes the manifold, the first piston chamber, the second piston chamber, the delivery port and the actuation control are part of a single-use or limited-use fluid-handling portion. In general, the fluid-handling portion may be configured to couple to the reusable handle portion including the power supply (alternatively, a power cord or wire may be used).

Any of these apparatuses may include a return bias (e.g., spring or springs, etc.) to return the function selection piston to a distal position when the actuation control is released. In some cases the return bias may be part of the actuation control which is, in turn, coupled to the selection piston, so that returning the actuation control to an initial (rest) position may restore the selection piston distally. Optionally or additionally, a return bias may be coupled to the selection piston direction itself.

For example, described herein are systems for injecting a fluid that may include: a manifold, wherein the manifold comprises a selection channel, a function selection piston that is configured to move within the selection channel, and a plurality of check valves; a first piston chamber fluidically connected to the selection channel of the manifold and in fluid communication with a reservoir port; a second piston chamber fluidically connected to the selection channel of the manifold in fluid communication with the reservoir port; a delivery port fluidically connected to the selection channel of the manifold; an aspiration window between the delivery port and the selection channel configured to display aspirated material; a trigger configured to drive the function selection piston within the selection channel so that activating the trigger initially retracts the function selection piston proximally away from the delivery port to aspirate material into the delivery port, and sustaining activation of the trigger retracts the function selection piston further proximally in the selection channel to fluidly connect the first piston chamber and the second piston chamber with the delivery port so that fluid is pumped out of the delivery port from the first piston chamber and the second piston chamber.

Also described herein are methods of injecting a material (e.g., fluid, suspension, etc.) into a patient using any of these apparatuses. For example, a method of injecting a fluid using a hand-held injector system that includes a manifold, a first piston chamber, a second piston chamber, and an actuation control, may include: actuating the actuation control to drive a function selection piston proximally within a selection channel of the manifold so that material is aspirated into a region of the selection channel having a transparent window from a needle fluidly coupled to the selection channel; and continuing to actuate the actuation control to move the function selection piston further proximally within the selection channel to fluidly connect the first piston chamber and the second piston chamber with the delivery port through the selection channel, wherein continuing to actuate the actuation control activates a drive assembly to drive reciprocation of a first piston in the first piston chamber and a second piston in the second piston chamber, pumping fluid out of the needle while alternately transferring fluid from a reservoir into the first piston chamber and the second piston chamber.

Any of these methods may include coupling the reservoir to the hand-held injector system. For example, a syringe (e.g., 60 cc syringe, etc.) of material may be attached, via leur lock, to the injector.

The methods described herein may include assembling the hand-held injector system, for example by attaching the fluid-handling portion to the handle portion. In some examples this may include coupling a fluid-handling portion comprising the manifold, the first piston chamber, the second piston chamber, and the trigger to a reusable handle portion including a power supply and the drive assembly to form the hand-held injector system.

In use, any of these methods may include determining blood was aspirated when actuating the trigger. For example, the method may include observing the aspiration window or aspiration region of the device to determine when blood is aspirated after first operating the actuation control. As mentioned above, actuating the actuation control may be actuated by pulling a trigger, pushing a button, etc. In any of these methods, the method may include restoring the function selection piston to a distal position after the actuation control is released.

Fluid may be pumped (injected) out of the needle in a continuous and/or pulsatile manner. In some examples fluid may be continuously pumped while the user is actuating the actuation control (e.g. pulling the trigger), so long as there is fluid available (including in the reservoir). In some examples pumping fluid out of the needle comprises continuously pumping fluid out of the needle. Alternatively, the apparatus may include control circuitry that meters the amount of fluid (e.g. by volume, and/or by time injecting) once the actuation control is actuated. In some examples one or more sensors may provide feedback based on the amount of fluid pumped and/or the duration of actuation.

In general, the method and apparatuses for injecting material described herein may be implemented as part of (or may include one or more parts, configurations, or components, and may generally improve upon) the apparatuses and methods described in PCTUS2021025868, herein incorporated by reference in its entirety.

Also described herein are apparatuses and methods for providing nerve stimulation and delivering a pharmaceutical to a patient. More specifically, this disclosure relates to controllably delivering electrical energy to a region of the patient to verify an injection location, aspirating the region, and then injecting a fluid, such as an injectable pharmaceutical, into the region.

One innovative aspect of the subject matter described in this disclosure may be implemented as an aspiration and injection device that may include a controller and an injection wand. The controller may include a dispensing unit configured to controllably displace a liquid pharmaceutical through an elongate tube and a control unit coupled to the dispensing unit and configured to cause the dispensing unit to displace the liquid pharmaceutical. The injection wand may be coupled to the elongate tube and include a needle tip and a handle configured to control aspiration from and liquid pharmaceutical deliver to a patient via the needle tip.

In some embodiments, the dispensing unit may include a pump configured to positively and negatively displace the liquid pharmaceutical. The handle may include a switch configured to cause the pump to positively and negatively displace the liquid pharmaceutical.

In some variations, the controller may be configured to monitor and control a pressure of the liquid pharmaceutical. In some other variations, the controller may be configured to monitor and control a flow rate of the liquid pharmaceutical. In still other variations, the controller may be configured to monitor and control a flow resistance associated with the liquid pharmaceutical.

In some embodiments, the controller may include visual indicators of at least one of a pressure, a flow rate, and a flow resistance. In some other embodiments, the injection wand may include a section configured to allow a clinician to determine whether blood is present in the aspirated fluid.

In some variations, the handle may include a plunger configured to aspirate fluid from the needle tip and enable the liquid pharmaceutical to flow into the needle tip from an input port. In some other variations, the control unit may be configured to be separable from the dispensing unit.

In some embodiments, the dispensing unit includes one or more syringes to contain and displace the liquid pharmaceutical. In some other embodiments, the dispensing unit may include a pump configured to provide positive and negative displacement of the liquid pharmaceutical.

In some variations, the injection wand is further configured to deliver electrical energy to the patient through the needle tip. The handle may further be configured to control the delivery of the electrical energy.

In some embodiments, the controller may be configured to be attached to an intravenous (IV) stand. In some other embodiments, the controller may be configured to be powered by at least one of a battery and alternating current (AC) power. In further embodiments, the needle tip may be a spinal needle.

Another innovative aspect of the subject matter described in this disclosure may be implemented as a method for delivering a liquid pharmaceutical to a patient. The method may include inserting a needle tip into a treatment area, negatively displacing, with a pump, a liquid pharmaceutical from the needle tip to aspirate fluid from the patient, and positively displacing, with the pump, the liquid pharmaceutical to injection the liquid pharmaceutical to the patient.

In some variations, the method may also include repositioning the needle tip after the pump negatively displaces the liquid pharmaceutical. In some other variations, the method may include delivering an electrical energy to the patient via the needle tip after the needle tip is inserted into the treatment area. In some other variations, the method may include repositioning the needle tip after delivering the electrical energy to the patient.

In some embodiments, the method may include delivering an electrical energy to the patient via the needle tip after the needle tip is inserted into the treatment area. The method may further include repositioning the needle tip in after delivering the electrical energy to the patient.

In some variations, the liquid pharmaceutical may be positively displaced at a predetermined pressure. In some other variations, the liquid pharmaceutical may be positively displaced at a predetermined flow rate. In still other variations, the liquid pharmaceutical may be positively displaced with respect to a predetermined flow resistance.

Any of the apparatuses described herein may be configured to select between a reciprocating drive belt and a one-direction drive belt.

Any of these apparatuses may be configured to heat or warm the material to be injected (e.g., warm to a preset value, such as body temperature (e.g., 37 degrees C., or higher or lower).

All of the methods and apparatuses described herein, in any combination, are herein contemplated and can be used to achieve the benefits as described herein.

BRIEF DESCRIPTION OF THE DRAWINGS

A better understanding of the features and advantages of the methods and apparatuses described herein will be obtained by reference to the following detailed description that sets forth illustrative embodiments, and the accompanying drawings of which:

FIGS. 5A-5C show another embodiment of a handle, in accordance with some embodiments.

FIG. 25A shows the selection piston within a selection channel of the manifold in a first (resting, non-actuated) configuration, fully distally extended in the selection channel. FIG. 25B shows the selection piston at a second position within the selection channel, drawing aspiration into the distal end (e.g., aspiration window) region of the selection channel. FIG. 25C shows the selection piston at a fully activated position, proximally retracted in the selection channel, so that the first and second piston chambers are in fluid communication with the delivery port for injection of fluid.

DETAILED DESCRIPTION

Various implementations relate generally to a method and apparatus for verifying a location to receive an injection, and then injecting a pharmaceutical into the patient at the verified location. More particularly, some implementations of the apparatus may include a controller and a wand. The wand may include a needle tip that may be used both for providing electrical energy to stimulate a patient's nerve as well as injecting the liquid pharmaceutical into the patient. Stimulation of a patient's nerve may be used verify the location to inject the pharmaceutical. In some embodiments, the wand may include a user-operated control that enables the electrical energy to be delivered to the needle as well as aspirate and inject the pharmaceutical.

Particular implementations of the subject matter described in this disclosure can be implemented to realize one or more of the following potential advantages. In some embodiments, the described techniques and apparatus may be used to reduce the required equipment used to both verify an injection location as well as deliver the injection. In some cases, a single clinician may be able to perform these tasks which conventionally required two or more clinicians. Furthermore, a reduction in the equipment that is used to verify the injection site and deliver the injection may reduce crowding in operating rooms or other treatment venues.

Figure 1:
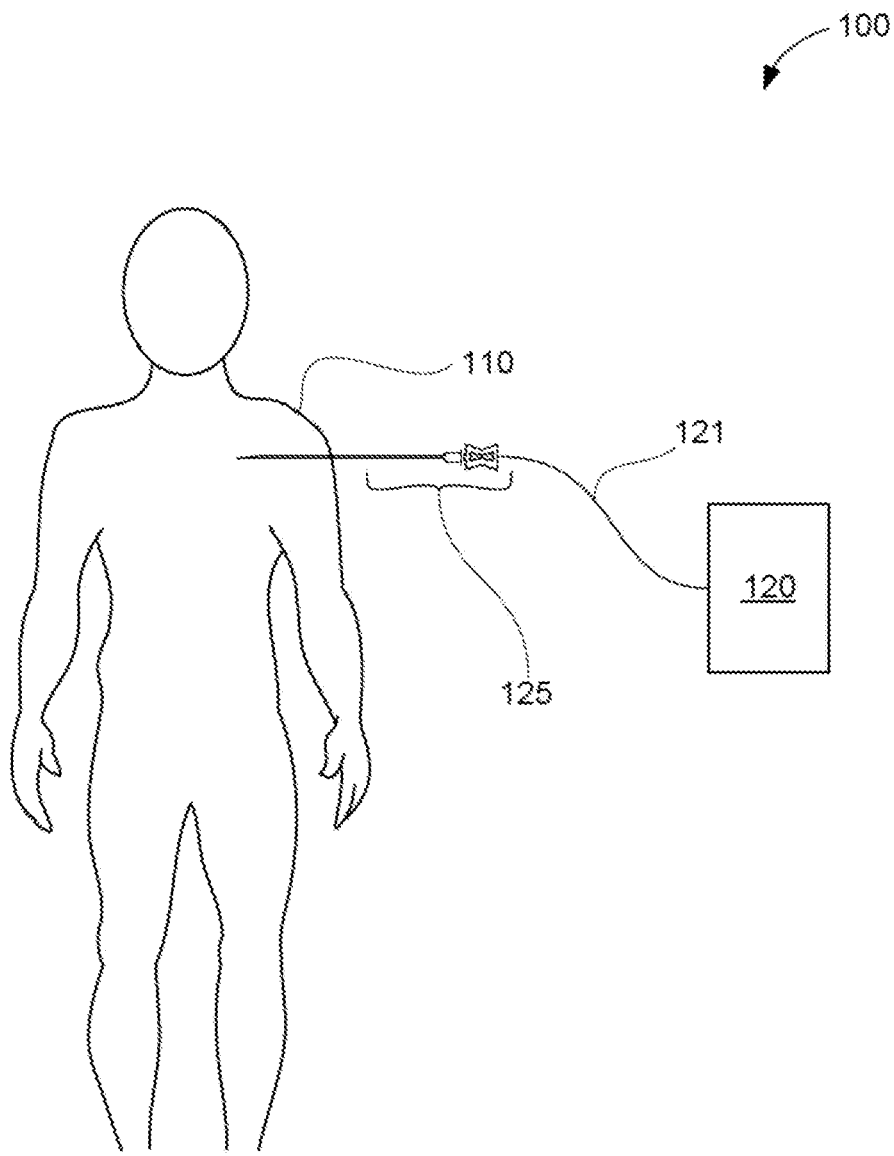
FIG. 1 depicts one example of an aspiration and injection system 100.

FIG. 1 depicts one example of an aspiration and injection system 100. As shown, the aspiration and injection system 100 may include a controller 120, an elongate tube 121, and an injection wand 125. The aspiration and injection system 100 may be used to deliver (e.g., inject) liquids, such as liquid pharmaceuticals, to a patient 110. The injection wand 125 may be coupled to the elongate tube 121, which in turn may be coupled to the controller 120.

The controller 120 may include one or more reservoirs to hold and contain the liquids for delivery to a treatment area. In some embodiments, the controller 120 may include a pump or other means for forcing (displacing) the liquid pharmaceutical through the elongate tube 121 and into the injection wand 125. The controller 120 is described in more detail below in conjunction with FIGS. 2, 6, and 7.

The injection wand 125 may be used to direct the liquid pharmaceutical from the controller 120 to a verified treatment area. In some embodiments, the injection wand 125 may include a handle and one or more switches (not shown here for simplicity) that are communicatively coupled to the controller 120. The handle and/or switches may enable a clinician to control actions of the injection wand 125 and the controller 120.

The clinician may operate the aspiration and injection system 100 in a first mode and cause the injection wand 125 to aspirate (e.g., withdraw fluid) from the patient 110. Aspiration may be used to confirm location of a tip of the injection wand 125. For example, if during aspiration blood is seen within a transparent portion of the injection wand 125, then the location of the tip of the delivery needle may be incorrect for the delivery of certain pharmaceuticals. In such cases, the clinician could reposition the injection wand 125.

The clinician may operate the aspiration and injection system 100 in a second mode and cause the injection wand 125 to deliver a pharmaceutical liquid contained in the controller 120 through the injection wand 125 to the patient 110. In some embodiments, the controller 120 may include a pump or similar device to force (displace) a liquid pharmaceutical through the elongate tube 121 and to the injection wand 125. In some embodiments, the liquid pharmaceutical may be controllably delivered to the patient 110 at a predetermined pressure, flow rate, or delivered according to a flow resistance.

In some cases, in order to verify the treatment area, the clinician may use a needle or other metallic object to introduce electrical energy (e.g., a current and/or a voltage)

to the patient. Upon delivery of the electrical energy, the clinician may monitor the patient for a response that would indicate that the needle or other metallic object is in the desired location. For example, as the needle delivers electrical energy, the clinician may monitor the patient to determine whether an expected muscular or nerve response occurs. In some cases, the observation of an expected muscular or nerve response may confirm the position of the needle. Upon confirmation of the needle position, the liquid pharmaceutical may be injected into the treatment area.

The clinician may operate the aspiration and injection system 100 in a third mode and cause the controller 120 to provide electrical energy to the injection wand 125. The clinician may then observe the patient to see if there is an expected response that could confirm the position of the injection wand 125. The third mode may be optional as in some cases precise and pinpoint location of the injection wand 125 may not be necessary. For example, if a simple intra-muscular or subcutaneous injection is needed, then a pinpoint location of the injection wand 125 may not be necessary. The injection wand 125 is described in more detail below in conjunction with FIGS. 2-5.

Thus, the aspiration and injection system 100 may provide an easy to use and compact pharmaceutical delivery system. The controller 120 may advantageously controllably deliver any liquid pharmaceutical, including viscous pharmaceuticals, at a predetermined pressure, flow rate, or based on a flow resistance. Through the injection wand 125, the clinician may control the liquid pharmaceutical injection without relying on a separate clinician to work syringes, pumps, or the like while at the same time controlling position of the injection wand 125. Furthermore, by delivering electrical energy through the injection wand 125 to verify needle position, use of a separate piece of medical equipment is avoided.

Figure 2:
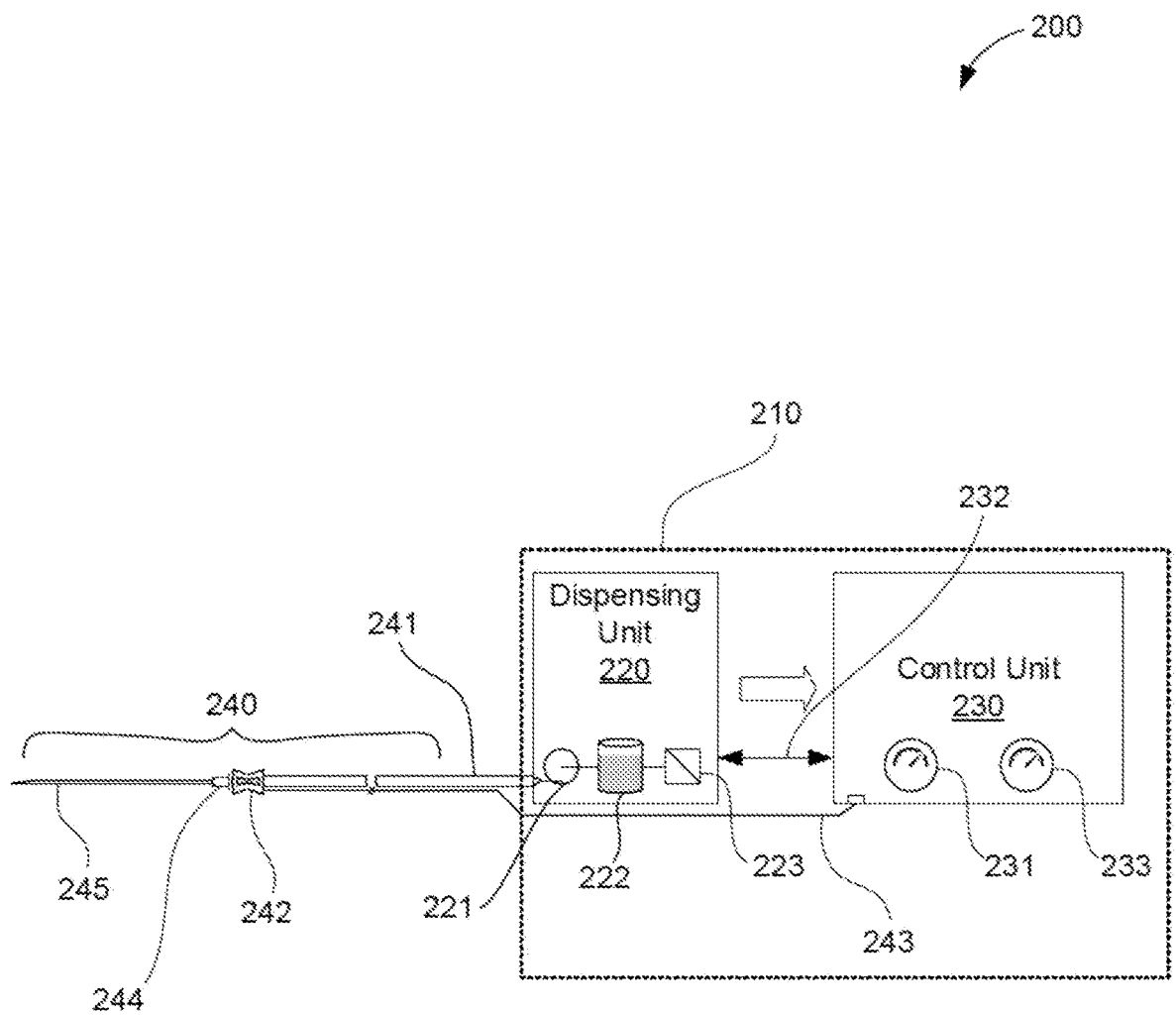
FIG. 2 is a simplified diagram of an aspiration and injection system, in accordance with some embodiments.

FIG. 2 is a simplified diagram of an aspiration and injection system 200, in accordance with some embodiments. The aspiration and injection system 200 may be an example of the aspiration and injection system 100 of FIG. 1. The aspiration and injection system 200 may include a controller 210 and an injection wand 240. (Note that the injection wand 240 is not drawn to scale. This illustration is meant to be used for explanatory purposes and not meant to be limiting.) As shown, the controller 210 may include a dispensing unit 220 and a control unit 230. In some embodiments, the dispensing unit 220 may attach or otherwise be coupled to the control unit 230 to form an integral controller 210. The dispensing unit 220 may include a pump 221, a reservoir 222, and a transducer 223. The reservoir 222, depicted as a container for simplicity, may contain the liquid to be injected into the patient through the injection wand 240. The liquid, which may be any feasible liquid including any liquid pharmaceutical (drug, saline, or a combination thereof), may be contained within a bag, vail, one or more syringes, or any other feasible containment vessel.

The reservoir 222 may be coupled to the pump 221. The pump 221 may directly or indirectly displace the liquid in the reservoir 222 through an elongate tube 241 to the injection wand 240. Example pumps 221 may include peristaltic pumps, piston pumps, or any other feasible liquid pump. The pump 221 may provide positive and/or negative displacement of the liquid.

In some variations, and without loss of functionality, one or more components of the dispensing unit 220 may reside instead, at least in part, in the control unit 230. In some variations, the pump 221 may be separated into two sections (not shown for simplicity) that includes a driving part and a driven part. For example, a first section in the dispensing unit 220 may include a driven part that physically contacts the liquid. A second section in the control unit 230 may include a driving part that can physically drive the driven part in the first section. In some cases, the dispensing unit 220, the elongate tube 241, and/or the injection wand 240 may be disposable. That is, components of the aspiration and injection system 200 that come into contract with the pharmaceutical fluid or the patient's blood may be sterilized prior to use and discarded after use. In contrast, the control unit 230, which may house more expensive components, may be reused multiple times.

Positive displacement may refer to liquid displacement away from the dispensing unit 220 (e.g., toward the injection wand 240) and negative displacement may refer to liquid displacement toward the dispensing unit 220 (e.g., away from the injection wand 240). The transducer 223 may be coupled directly or indirectly to the reservoir 222 and/or the pump 221. In some variations, the transducer 223 and may measure pressure associated with the liquid being displaced through the elongate tube 241. In some other variations, the transducer 223 may measure flow rate or determine a flow resistance of the liquid being displaced. The transducer 223 may be coupled to the control unit 230 through a coupling 232. The coupling 232 may be a wired or wireless coupling that may enable the dispensing unit 220 to be separated from the control unit 230.

The control unit 230 may control operations of the dispensing unit 220. For example, the control unit 230 may directly or indirectly control the pump 221 in the dispensing unit 220. In some embodiments, the control unit 230 may monitor pressure and/or flow rate via the transducer 223 and control the pump 221 to maintain a predetermined pressure and or flow rate. The predetermined pressure or flow rate may be controlled or determined by a clinician.

In some embodiments, the dispensing unit 220 and/or the control unit 230 may be configured to be hung from an intravenous (IV) stand or pole. In some cases, hanging components from an IV stand may enable easy use in various medical settings. In some other embodiments, the dispensing unit 220 and/or the control unit 230 be configured to be placed on a desk or table.

The injection wand 240 may include the elongate tube 241, a handle 242, and a needle tip 245. The injection wand 240 may be coupled to the controller 210 via the elongate tube 241 and one or more electrical conductors 243. As liquid is displaced from the dispensing unit 220 (in some cases displaced by the pump 221), the liquid may travel through the elongate tube 241 and to the injection wand 240. The needle tip 245 may allow the liquid to be delivered to a subcutaneous location, an intra-muscular location, or any other feasible patient location. In one embodiment, the aspiration and injection system 200 may be used to inject a spinal nerve blocking pharmaceutical. In that case, the needle tip 245 may be a spinal needle.

The handle 242 may be coupled to the control unit 230 through the one or more electrical conductors 243. The handle 242, which may include one or more switches, may enable the clinician to control operations of the aspiration and injection system 200. For example, the handle 242 may control operations of the pump 221 to control the delivery of fluids through the needle tip 245. In some embodiments, foot pedals or foot switches may be used in place of handle-based switches. In some other variations, the electrical conductors 243 may be replaced any feasible wireless connection. That is, radio-frequency(RF) and/or optical signals may be used to communicatively couple the handle 242 with the control unit 230. For example, an RF link (e.g., a Bluetooth link, a link conforming with any of the IEEE 802.11 family of standards, or any other feasible wireless communication protocol) may be used in place of, or in addition to the electrical conductors 243 to control the aspiration and injection system 200.

In other variations, the handle 242 may also enable the clinician to provide electrical energy to the injection wand 240. As described above with respect to FIG. 1, the clinician may use electrical energy to verify a location and/or position of the needle tip 245 prior to an injection of the liquid pharmaceutical. In some embodiments, the controller 210 (controlled by the handle 242) may deliver electrical energy to the needle tip 245 through the electrical conductors 243 to provoke a response in the patient. In some cases, if a response to the electrical energy is observed by the clinician, then the needle tip 245 position is verified.

In some variations, the control unit 230 may cause the pump 221 to negatively displace the liquid. In other words, the pump 221 may draw liquid from the injection wand 240 to aspirate fluid from the patient. By drawing fluid from the patient, the clinician may determine, at least in part, the position of the injection wand 240. For example, in some embodiments the injection wand 240 may include a transparent (or translucent) section 244. If the clinician sees an indication of blood in the transparent section 244, then the injection wand 240 may be positioned in or near a vein or artery which may be contraindicated for the pharmaceutical to be delivered.

In some variations, the control unit 230 may include a gauge 231 to provide a visual indication of the pressure of the liquid. For example, the gauge 231 may be coupled to the transducer 223 and provide a human readable indication of the output pressure of the liquid. Additionally, or alternatively, the control unit 230 may include a flow rate indicator 233 that provides a visual indication of the flow rate of the liquid. In some other variations, the control unit 230 may have an indicator of flow resistance (Lohm). Furthermore, in some embodiments the pressure, flow rate, and/or flow resistance may be indicated with a visual color indicator. For example, a green light may indicate that the monitored attribute (pressure, flow rate, flow resistance, or the like) is within an acceptable range. A yellow light may indicate that the attribute may be within a "warning" range. A red light may indicate that the monitored attribute is beyond of an acceptable range.

In some variations, the control unit 230 may be powered by "wall power." That is, power may be provided by plugging or otherwise connecting the control unit 230 to a conventional alternating current (AC) power source. In some other variations, the control unit 230 may include a battery (not shown) that may be charged to provide power for the aspiration and injection system 200. By including a battery, the aspiration and injection system 200 may be ambulatory and enable mobile use in many treatment environments.

Figure 3:
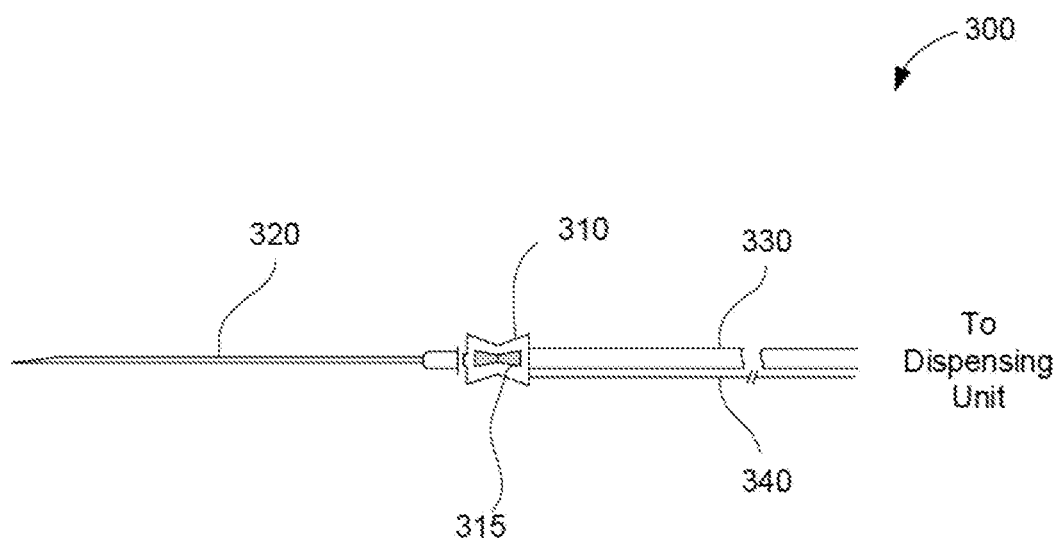
FIG. 3 shows a simplified diagram of an injection wand, in accordance with some embodiments.

FIG. 3 shows a simplified diagram of an injection wand 300, in accordance with some embodiments. The injection wand 300 may be an embodiment of the injection wand 240 of FIG. 2. The injection wand 300 may include a handle 310, a needle tip 320, an elongate tube 330, and electrical conductors 340.

The handle 310, which may be an embodiment of the handle 242 of FIG. 2, may provide an ergonomic surface with which the clinician can position the needle tip 320 in the patient and control fluid operations of the controller 210 (not shown). The handle 310 may be coupled to the controller 210 through the elongate tube 330 and the electrical conductors 340 (which may be embodiments of the elongate tube 241 and electrical conductors 243, respectively). In some embodiments, the handle 310 may include a cavity or tunnel that couples fluid to/from the elongate tube 330 to/from the needle tip 320.

Figure 4A:
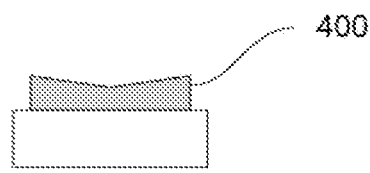
FIGS. 4A-4C show example side views of a switch.
Figure 4B:
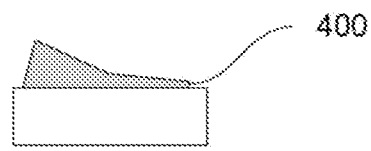
Figure 4C:
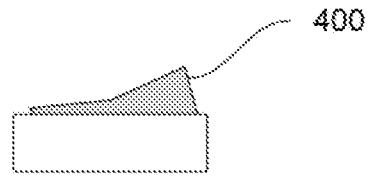

The needle tip 320, which may be an embodiment of the needle tip 245, may be removably coupled to the handle 310. In this manner, the clinician may select different needle tips that may be well suited for different applications. The handle 310 may include a switch 315 that may be coupled to the electrical conductors 340 to control a pump (not shown). For example, the switch 315 may enable aspiration and/or injection of a liquid pharmaceutical with respect to a patient. The switch 315 may also control delivery of electrical energy to the needle tip 320. In some embodiments, the handle 310 may not include the switch 315. Instead, functionality of the switch 315 may be provided by one or more foot switches or foot pedals. FIGS. 4A-4C show example side views of a switch 400. The switch 400 may be an embodiment of the switch 315 of FIG. 3. FIG. 4A shows the switch 400 in a neutral position. As described with respect to FIG. 2, the switch 400 may be coupled to and control the pump 221 in the controller 210 (pump and controller not shown). In the neutral position, the switch 315 may not actuate the pump in the controller 210. FIG. 4B shows the switch 400 in a first position. In some embodiments, when the switch 400 is in the first position, the pump 221 may negatively displace liquid and aspirate fluid from the patient. That is, the pump 221 may draw a liquid from the patient and enable the clinician to determine if there is any blood that is aspirated. FIG. 4C shows the switch 400 in a second position. In some embodiments, when the switch 400 is in the second position, the pump 221 may positively displace the liquid pharmaceutical from the reservoir 222 into the patient. That is, the pump 221 can inject the pharmaceutical into the patient.

In some variations, the switch 400 may be capable of a third position (not shown). In the third position, the pump 221 may not run, but the controller 210 may provide an electrical energy that may be provided to a needle tip to provoke a response from the patient.

FIGS. 5A-5C show another embodiment of a handle 500, in accordance with some embodiments. In contrast to other handles, the handle 500 may be solely or partially mechanical, and may include no electrical switches. Aspiration and injection operations may be controlled by a clinician moving or sliding a piston or plunger within the handle 500.

As shown in FIG. 5A, the handle 500 may include a housing 510, a finger grip 520, a piston 530, and a needle tip 540. The housing 510 may be formed from any feasible material including polypropylene or the like. Additionally, the housing 510 may be transparent or translucent. The housing 510 may include a port 515 that may receive the liquid pharmaceutical from a pump, such as the pump 221 of FIG. 2 (not shown). In some variations, the port 515 may be coupled to an elongate tube (also not shown) that delivers the liquid pharmaceutical to the handle 500. The needle tip 540 may be coupled to the housing 510.

The piston 530 may conform and fit within a bore 551 of the housing 510. The finger grip 520 may be coupled to the piston 530 and the finger grip 520 may be exposed through a surface of the housing 510 thereby being accessible by the clinician.

FIG. 5A shows the handle 500 in an initial arrangement. The finger grip 520 and the piston 530 may be positioned such that fluid flow from the port 515 is blocked. FIG. 5B shows the handle 500 in a second arrangement as the piston 530 moves away from the needle tip 540. For example, a clinician may move the finger grip 520, which is coupled to the piston 530, away from the needle tip 540. As the piston 530 moves away from the needle tip 540, fluid may be aspirated from the patient. This aspiration may enable the clinician to determine if the needle tip 540 is correctly positioned in the patient. For example, if blood is aspirated into the housing 510, then the needle tip 540 may be located in a vein or artery which may not be desirable. Note that in this position, the piston 530 still blocks fluid from the port 515.

FIG. 5C shows the handle 500 in a third arrangement as the finger grip 520 pulled further away from the needle tip 540. As shown, position of the finger grip 520 may cause the piston 530 to move further away from the needle tip 540 and allow fluid to flow from the port 515, into the housing 510, and through the needle tip 540. In this arrangement, the piston 530 no longer blocks fluid from the port 515.

Figure 6:
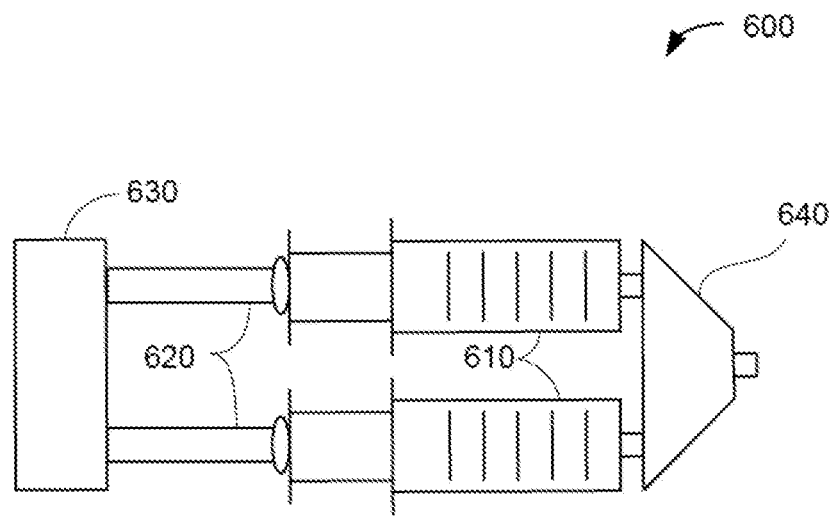
FIG. 6 is a simplified drawing of one embodiment of a pump, in accordance with some embodiments.

FIG. 6 is a simplified drawing of one embodiment of a pump 600, in accordance with some embodiments. The pump 600 may be an implementation of the pump 221 and the reservoir 222 as shown in FIG. 2. The pump 600 may include reciprocating pistons 610, a drive assembly 620, two or more syringes 630, and a manifold 640. In some embodiments, the pump 600 may be similar to one or more apparatus described in U.S. patent application Ser. No. 17/223,976 (now U.S. Pat. No. 11,229,750) entitled "Injection Device," the contents of which are incorporated by reference as if set forth fully herein. The two or more syringes 630 may be filled with a liquid pharmaceutical and then attached or otherwise coupled to the manifold 640. The manifold 640 may be coupled to a needle tip (not shown). The outputs of the syringes 630 may be collected by the manifold 640 and provided to the needle tip.

The syringes 630 may be any feasible size. In some variations, the syringes may be selected from any conventional syringe that may hold sufficient fluid to provide an effective therapy.

The drive assembly 620 may control the pistons 610 that, in turn, may be coupled to plungers of the syringes 630. The pistons 610 may move toward the syringes 630 thereby moving the plungers causing fluid to be expelled from the syringes 630. In some embodiments, the pistons 610 may move alternately, first advancing a first plunger, then advancing a second plunger. In some other embodiments, the pistons 610 may move together. In some embodiments, the drive assembly 620 may control pressure placed on plungers of the syringes 630 to provide a predetermined amount of pressure, and/or flow rate of fluid. In some other variations, a pressure transducer (not shown) may be coupled to the output of the manifold 640 to measure output pressure, flow rate, or the like.

Figure 7:
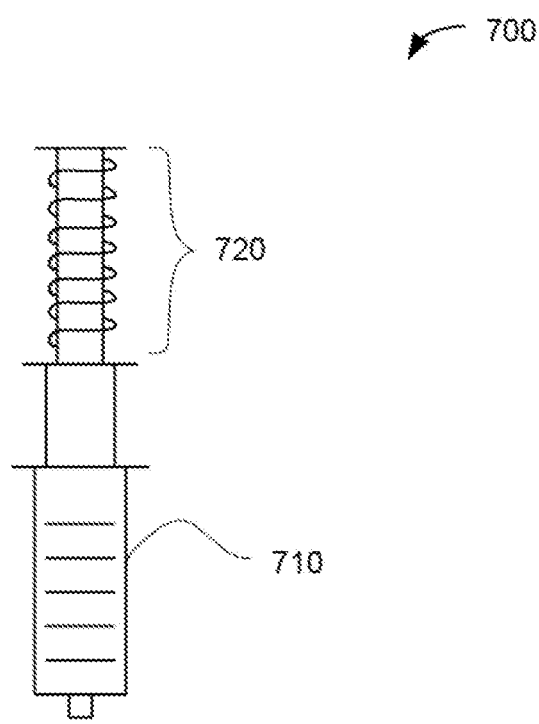
FIG. 7 is a simplified drawing of another implementation of a pump, in accordance with some embodiments.

FIG. 7 is a simplified drawing of another implementation of a pump 700, in accordance with some embodiments. The pump 700 may be an implementation of the pump 221 and the reservoir 222 as shown in FIG. 2. The pump 700 may include a syringe 710 and an actuator 720. The actuator 720 may be coupled to a plunger of the syringe 710. A needle tip (not shown) may be coupled to the syringe 710. The actuator 720 may be driven by springs or by other mechanical means including, but not limited to drive screws, lead screws, linear actuators, stepper motors, and the like. In some embodiments, the actuator 720 may control pressure on the plunger of the syringe 710 to provide a predetermined amount of pressure, and/or flow rate of fluid. In some other variations, a pressure transducer (not shown) may be coupled to the output of the syringe 710 to measure output pressure, flow rate, or the like.

Figure 8:
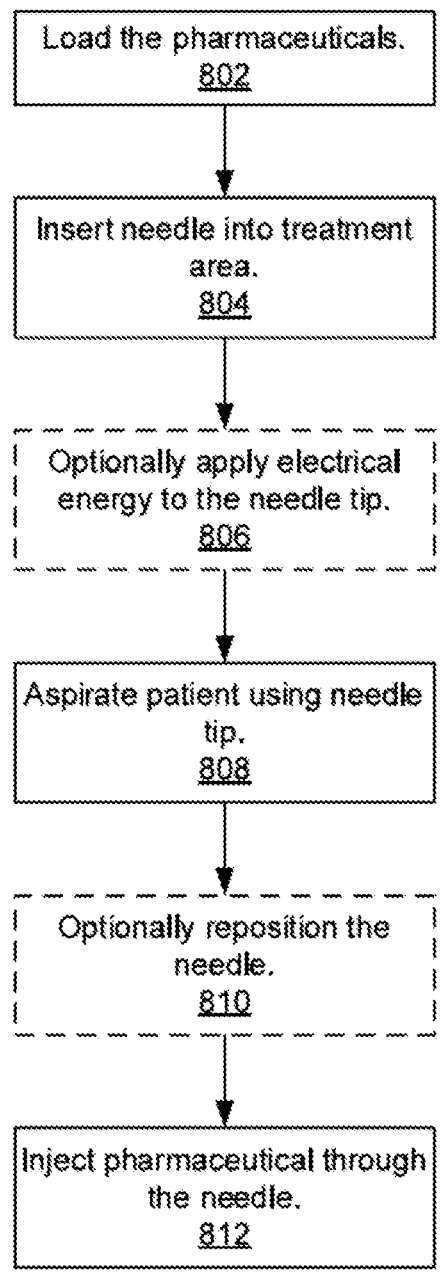
FIG. 8 is a flowchart depicting an example method for injecting a liquid pharmaceutical into a patient, in accordance with some embodiments.
Figure 9:
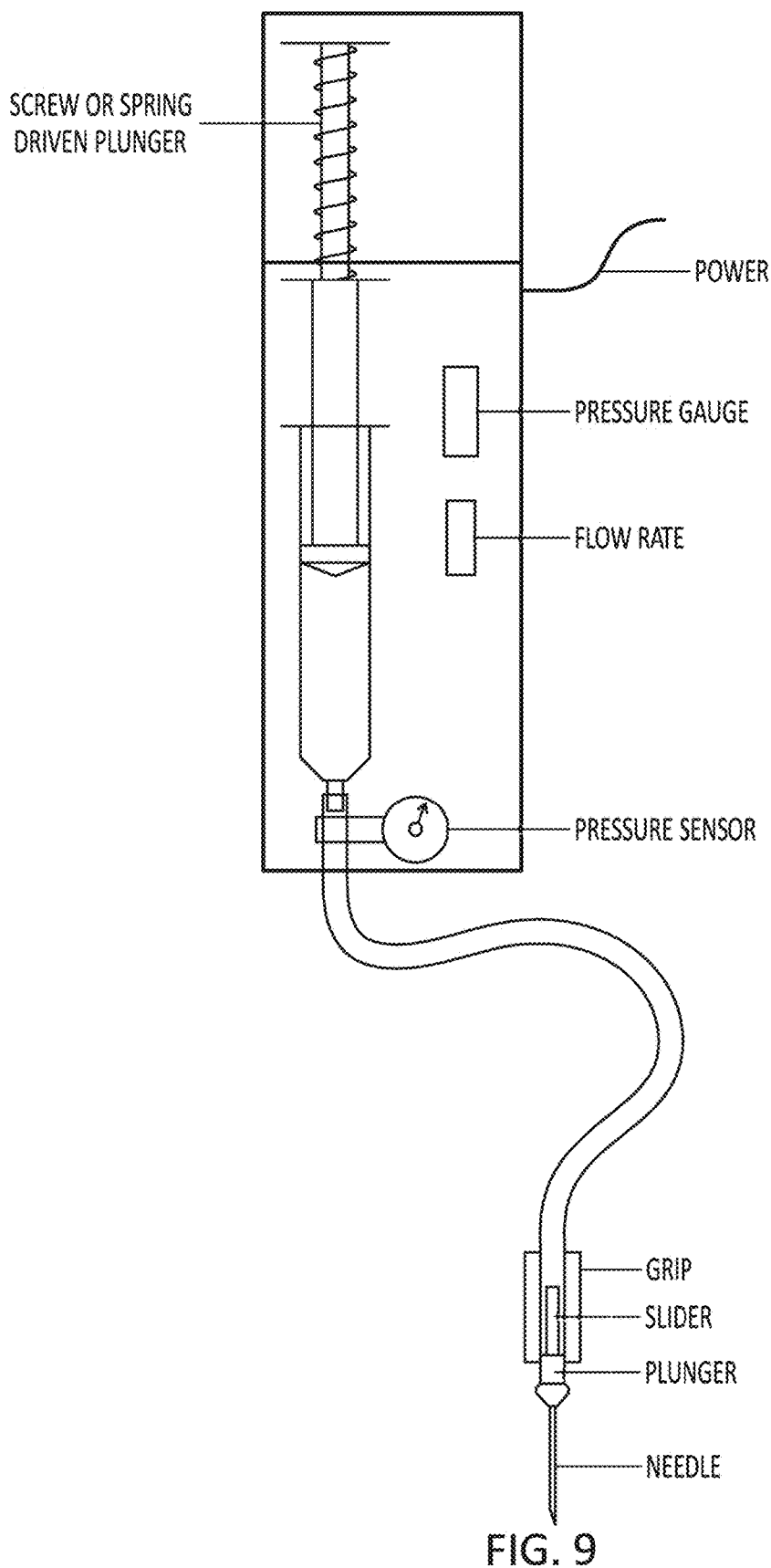
FIG. 9 is another example of an apparatus.
Figure 10:
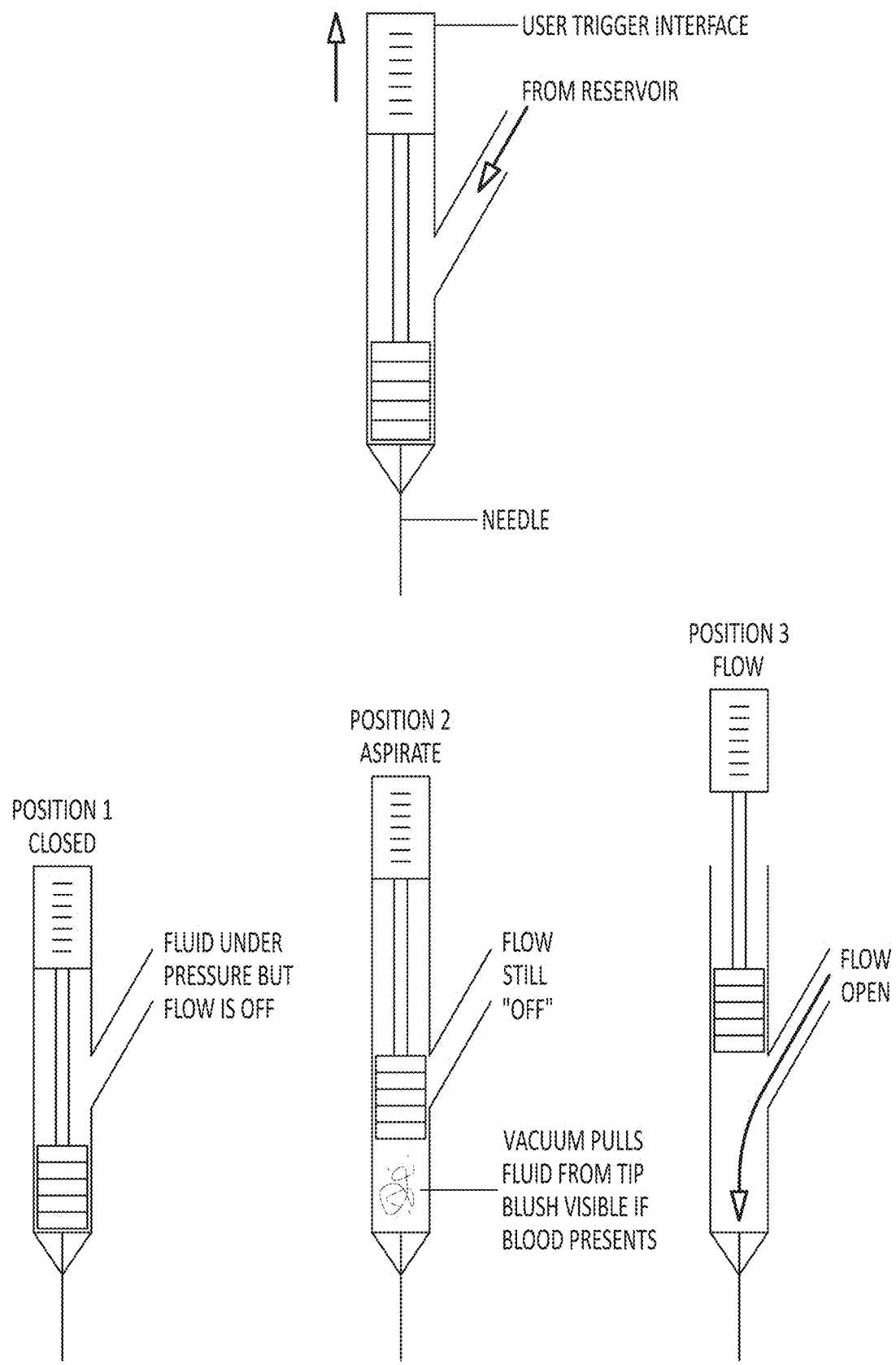
FIG. 10 illustrates another example.
Figure 11:
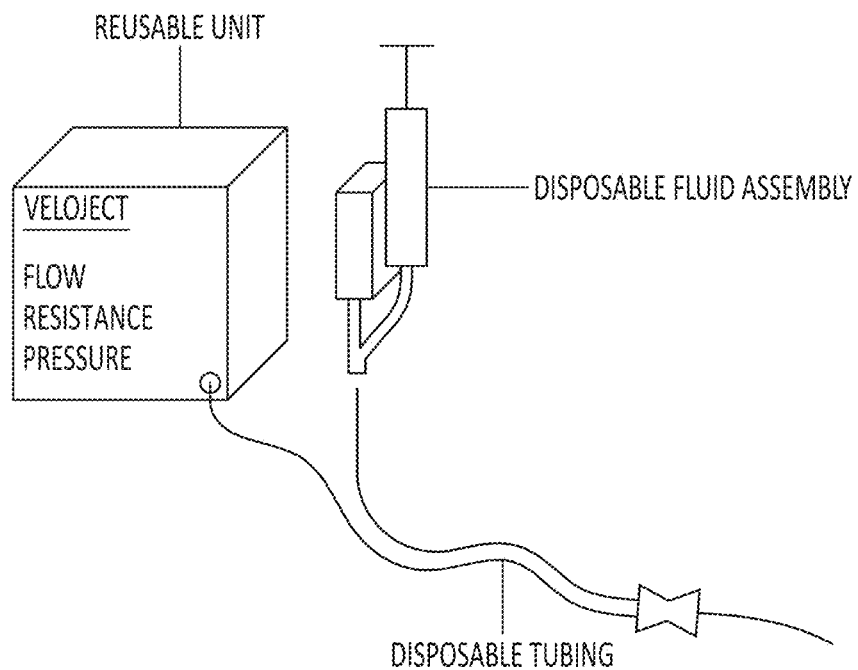
FIGS. 11 and 12 also illustrate examples.
Figure 12:
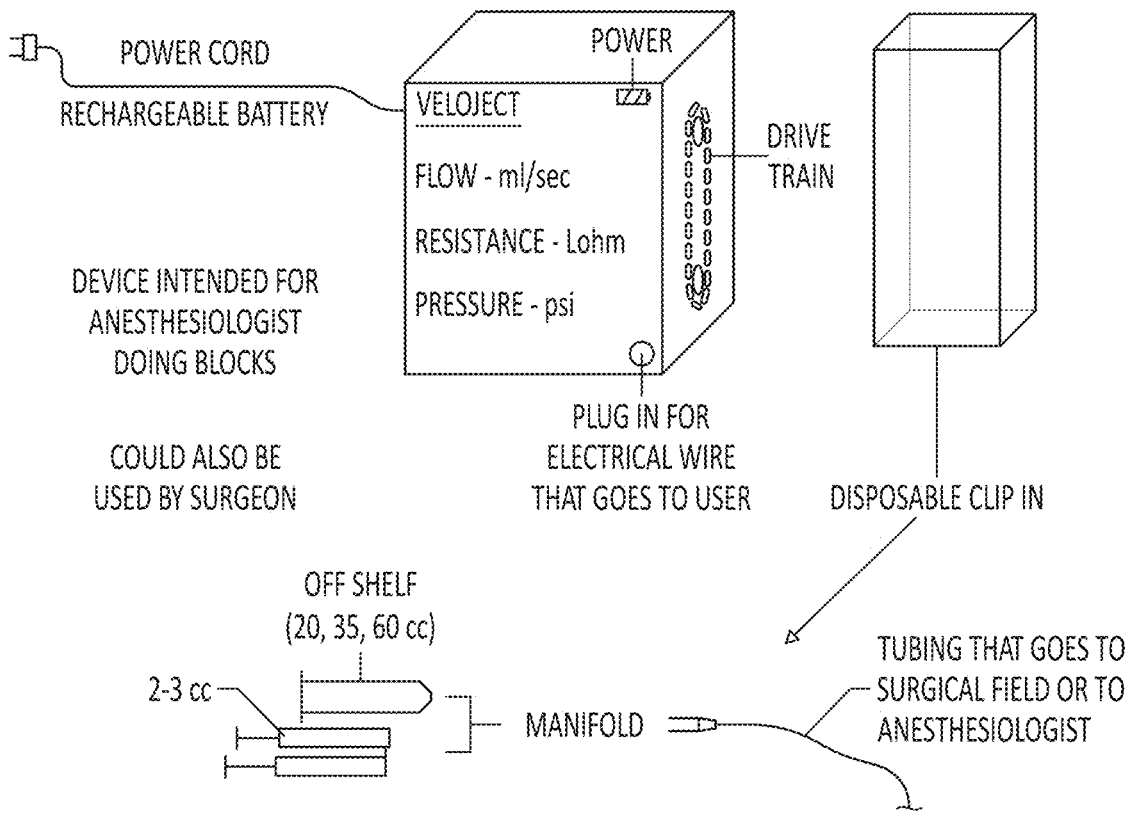

FIG. 8 is a flowchart depicting an example method 800 for injecting a liquid pharmaceutical into a patient, in accordance with some embodiments. Some examples may perform the operations described herein with additional operations, fewer operations, operations in a different order, operations in parallel, and some operations differently. The method 800 is described below with respect to the aspiration and injection system 200 of FIG. 2, however, the method 800 may be performed by any other suitable system or device.

The method 800 begins in block 802 as pharmaceuticals are loaded into the aspiration and injection system 200. For example, the liquid pharmaceuticals may be loaded into the reservoir 222. In some variations, the liquid pharmaceuticals may be loaded into one or more syringes that may be included within the aspiration and injection system 200.

Next, in block 804 the clinician may insert a needle into a treatment area. For example, the clinician may guide the injection wand 240 to insert the needle tip 245 into the patient. In one embodiment, the clinician may place the needle tip 245 near a nerve to be treated with a nerve blocker. In another embodiment, the clinician may place the needle tip 245 in a region to provide a subcutaneous or intra-muscular injection.

Next, in block 806 the aspiration and injection system 200 may optionally provide electrical energy to the needle tip 245. (Optional operations are shown in FIG. 8 with dashed lines.) While providing electrical energy, the clinician may observe the patient to determine whether there are any physical reactions (movements, twitches, etc.) in response to the electrical energy. In some cases, the physical reactions may indicate that the needle tip 245 is in the desired region. The electrical energy may be provided by the controller 210. Furthermore, the electrical energy may be provided in response to a user interaction with a switch, button, foot pedal, or the like.

Next, in block 808 the aspiration and injection system 200 may aspirate the patient with the needle tip 245. Aspiration may be used to verify, at least in part, the location of the needle tip. In some cases, if blood is aspirated from the patient, then the needle tip 245 may be placed incorrectly within the patient to receive the liquid pharmaceutical. Blood may be identified as being present by viewing the aspirate through a transparent or translucent portion of the injection wand 240. In some embodiments, the aspiration and injection system 200 may include a pump 221 that may negatively displace fluid to aspirate fluids from the patient. In some other embodiments, the aspiration and injection system 200 may include an injection wand that includes a plunger or piston that may be used to aspirate fluids from the patient.

Next, in block 810 the clinician may optionally reposition the needle tip 245. For example, if the presence of blood is identified during the aspiration of block 808, then the clinician may reposition the needle tip 245 in another location of the patient.

Next, in block 812, the aspiration and injection system 200 may inject the pharmaceutical into the patient. In some embodiments, the aspiration and injection system 200 may use a pump 221 to positively displace the liquid pharmaceutical from the reservoir 222 through the injection wand 240 and into the patient.

EXAMPLES

FIGS. 9-12 illustrate additional examples.

These apparatuses may facilitate the administration of local anesthetic into tissues of varying resistance in the operating room in an ergonomic, efficient, and precise manner. The apparatus was conceived after the realization that injecting large volumes of local anesthetic is difficult when using larger volume syringes and smaller bore needles, especially in tissues of varying resistance. Larger bore needles often create a path for the injected fluid to egress out of, which is counterproductive. The use of a lower volume syringe improves the ratio between the diameter of the syringe and the bore of the needle but does so at the expense of inefficient repetitive refilling of the smaller volume syringe.

These apparatuses may solve the problem of administering large volumes of local anesthetic. The apparatus may be an alternative to that shown in U.S. patent application Ser. No. 17/223,976, (now U.S. Pat. No. 11,229,750) herein incorporated by reference in its entirety, or may be incorporate features of that apparatus, and may be used by both use by Anesthesiologists and surgeons.

Anesthesiologists currently perform peripheral nerve blocks where they hold an ultrasound with one hand and a spinal needle with another. The spinal needle is connected to a syringe via a sterile tubing which is being operated by the OR nurse. The anesthesiologist has to rely on the nurse to aspirate, inject and report resistance. There is variability in terms of experience, strength, and reproducibility between nurses. This apparatus may solve this by providing a device that will provide the plunger pressure and aspiration allowing the anesthesiologist to control the flow during injection. The apparatuses describe herein can also be used for surgical indications. This may reduce the need to have a completely disposable unit or would reduce the need to re-sterilize the reusable portion in the modular design.

In some examples the device has 3 portions: REUSABLE UNIT, DISPOSABLE FLUID ASSEMBLY, DISPOSABLE TUBING. The device may have a REUSABLE UNIT that is non-sterile, able to be anchored (e.g., to an IV pole or Ultrasound machine), with a re-chargeable battery. The device may have a DISPOSABLE FLUID ASSEMBLY that will house two pistoning syringes (e.g., syringe volumes of 1 cc, 2 cc, 3 cc, etc.), a fluid manifold, and a connector that will be compatible with an off the shelf syringe that has a Leur port. The mechanism of the pistoning syringes has been described and validated before (e.g., U.S. patent application Ser. No. 17/223,976, now U.S. Pat. No. 11,229,750). The DISPOSABLE FLUID ASSEMBLY is meant for a one-time use per patient.

In an alternate embodiment, the apparatus may provide pressure to a single large reservoir instead of the two pistoning syringes. The force may be applied by a spring, screw or other mechanical means.

The device may have DISPOSABLE TUBING that may connect to the DISPOSABLE FLUID ASSEMBLY to the needle being used by the anesthesiologist or surgeon. Along with this tubing will be a disposable CABLE that will connect to the REUSABLE UNIT. At the end of the DISPOSABLE TUBING will be an ergonomic material so that the user can firmly hold the needle and will allow for precise placement of the needle. On the ergonomic portion of the DISPOSABLE TUBING will be a button that can be manually pushed to allow for aspiration or injection. Pressing this button will communicate to the REUSABLE UNIT via the disposable CABLE that is part of the DISPOSABLE TUBING. This will allow the user to activate the device, allowing them to aspirate or inject.

In an alternate example, the device may not have the disposable CABLE if the aspirate feature is built into the trigger mechanism in the user's hand. The aspirate feature may be accomplished by a plunger in the flow path that pulls a small vacuum at the tip as the user activates the pumping. The initial translation of the trigger will aspirate, and the end of the travel will open the flow path and activate the pump.

Figure 22:
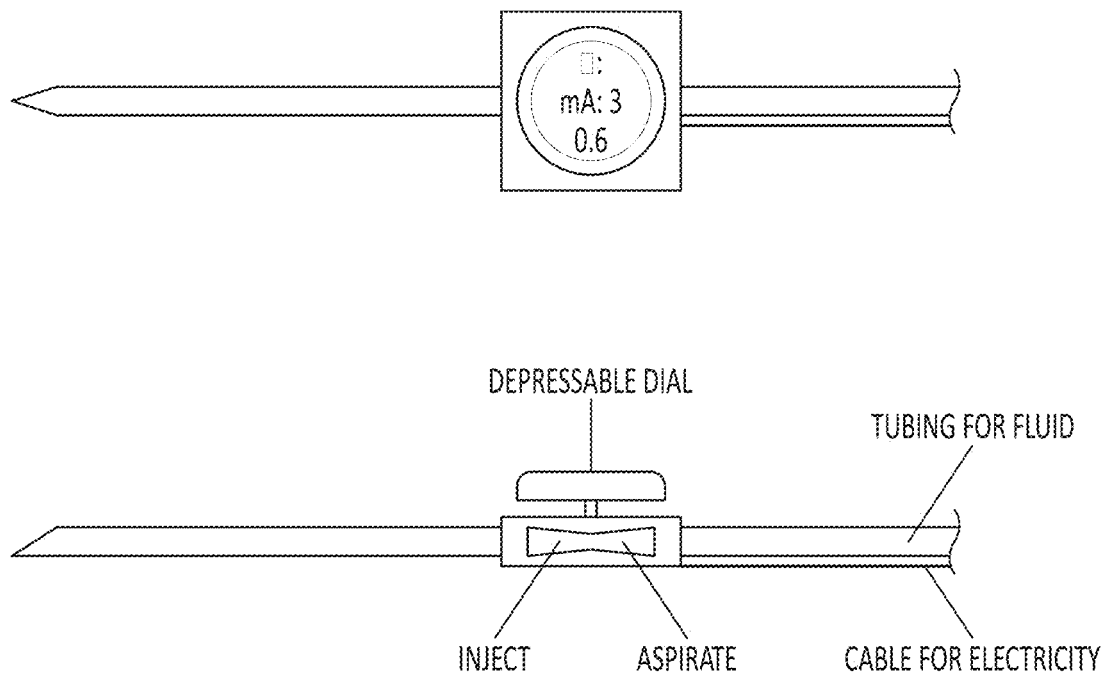
FIG. 22 illustrates an example of an injection wand as described herein.
Figure 22:
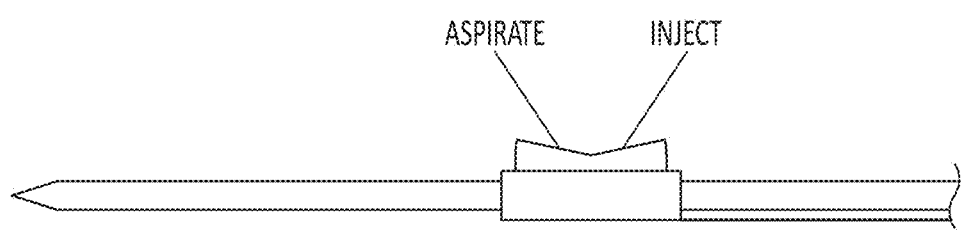

FIG. 22 shows an example of a handle/control. FIG. 22 shows a dial that can be turned to varying the electricity (mA), as well as the aspirate/inject button. This may connect to a spinal needle and may be a continuation of a tube for fluid passage alongside a cable for electricity conduction.

The reusable base that may house the motor/battery/power and can be mounted to an IV pole, be freestanding, or mount to an ultrasound will have a display that can tell users numerically: Flow (ml/sec), resistance (ohms), electrical current (mA), volume dispensed (ml), and battery life. Beneath flow, resistance, and electrical current may include visual indicators (e.g., green, yellow and red) to help visualize these numbers. There will be a dial net to electrical current to provide another way for electrical current to be adjusted, initiated and ceased. There may be a way to initiate the device (inject, aspirate, speed of aspiration) in the event that the controls held be the user are non-functioning.

The disposable part that will attach to the reusable base can include one of the following mechanisms of action: a pistoning syringe design (see below), a peristaltic pump, a lead screw, and/or any other mechanism. The tubing that connects can be just a tube for injection/aspiration or a tubing (for injection/aspiration) that can have an adjacent cable for electrical stimulation. The aspiration, injection hand button can have the ability to increase the speed of the motor so as to control the flow rate.

Aspiration Features

Any of the apparatuses herein may include an injection trigger that may have a built-in aspirate feature that is activated by a short pull on the trigger. The user can then determine if the tip of the needle is not in the vascular system and can proceed to pull the trigger back fully to open the fluid path and activate the pumping mechanism.

The triggering mechanism may have three states, closed, aspirate, and open, controlled by the trigger mechanism. The mechanism is in the path of the fluid flow with a sealed plunger like a common syringe plunger that moves inside the fluid path to restrict flow, pull a vacuum, or open the fluid path. The trigger has a lever arm. The trigger may be configured to close the flow. In the closed state, the fluid pressure is maintained in the line and the reservoir syringe. The fluid is prevented from flowing through the needle by a physical stopper in the line at the needle tip.

The trigger may be configured to be set to aspirate. For example the user may pull the trigger back a small amount (2-3 mm). This pulls fluid back into a clear portion of the fluid path adjacent to the needle luer lock connection. This is visible to the user, and it is possible to assess if the fluid contains blood. The fluid path is still closed in this state so that the medication cannot flow though into the patient.

The trigger may be configured to be set to open. The user, after confirming that the needle tip is not in the vascular system, may advance the trigger mechanism to the open flow position which allows the mediation to freely flow through the needle into the patient. The flow may be maintained by the constant pressure in the system applied to the plunger of the syringe. The system remains open until the user releases the trigger which will return the trigger to the closed position. Se FIG. 13 for an illustration of one example of these states.

In some examples, the system consists of a reservoir syringe that is loaded onto a device that creates a positive constant pressure. The device user interface includes a pressure gauge and display and flow rate measurement and indicator. A tube leads from the pressurized syringe to the user's hand. The user holds a component that has the needle and the ability to aspirate and to release the flow of the anesthetic.

The triggering mechanism may have three states, closed, aspirate, and open, controlled by a sliding trigger mechanism. The mechanism is in the path of the fluid flow with a sealed plunger similar to a common syringe plunger that moves inside the fluid path to restrict flow, pull a vacuum, or open the fluid path. These states are:

(1) Closed. In the closed state, the fluid pressure is maintained in the line and the reservoir syringe. The fluid is prevented from flowing through the needle by a physical stopper in the line at the needle tip.
(2) Aspirate. The user pulls the trigger back a small amount (2-3 mm). This pulls fluid back into a clear portion of the fluid path adjacent to the needle luer lock connection. This is visible to the user, and it is possible to assess if the fluid contains blood. The fluid path is still closed in this state so that the medication cannot flow though into the patient.
(3) Open. The user, after confirming that the needle tip is not in the vascular system, advances the trigger mechanism to the open flow position which allows the mediation to freely flow through the needle into the patient. The flow is maintained by the constant pressure in the system applied to the plunger of the syringe. The system remains open until the user releases the trigger which will return the trigger to the closed position. See, e.g., FIGS. 9 and 10.

Collapsible Spring-Loaded Plunger

Figure 14:
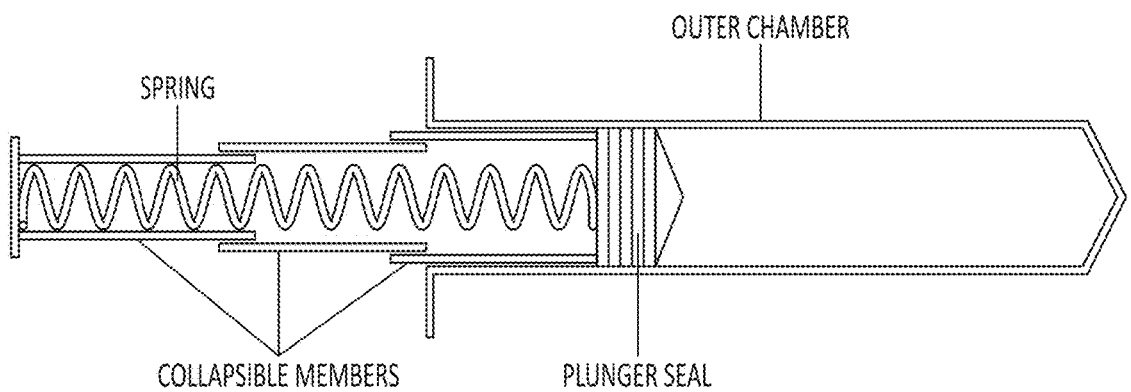
FIG. 14 illustrates another example of an apparatus as described herein.

Syringe plungers are rigid members that can pull and push the seal component inside the cylinder to draw fluid in and ush fluid out of a syringe. The plungers are single piece rigid columns. In one design (see, e.g., FIG. 14) the plunger is composed of a series of stacking members that can collapse down to a shorter final state. Inside the collapsible members is a spring mechanism that is compressed. The collapsed plunger is secured to a feature on the outer cylinder of the syringe to create a positive pressure within the syringe. This compressed state will push the plunger down and pressurize the fluid in the chamber to push the fluid out the exit port. The collapsed plunger provides this mechanical advantage and reduces the bulk of the syringe.

Auto Recharging Small Bore Syringe

Figure 15:
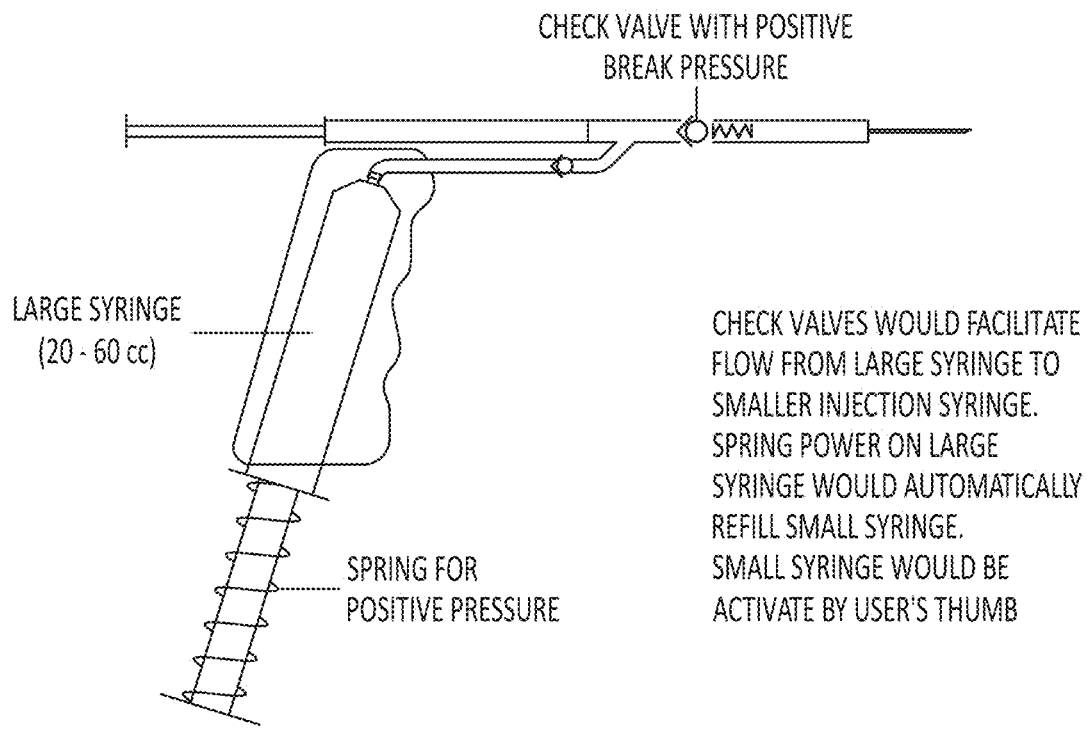
FIG. 15 is an example of an injection apparatus as described herein.

A larger syringe, 20-60 cc, may be used to repeatedly refill a single small-bore syringe which is injected into the patient. See, e.g., FIG. 15. The small-bore syringe does not require a large amount of force to push the plunger. The plunger of the small bore may be activated by the user's index finger to pulling a long stroke trigger. Or in another version the user's thumb is used to push the plunger. The return stroke of the small-bore syringe is accomplished by pressure in the large-bore syringe applied by a spring mechanism. A check valve in the fluid path prevents the small-bore syringe flow from returning the fluid back into the large-bore syringe.

Figure 16:
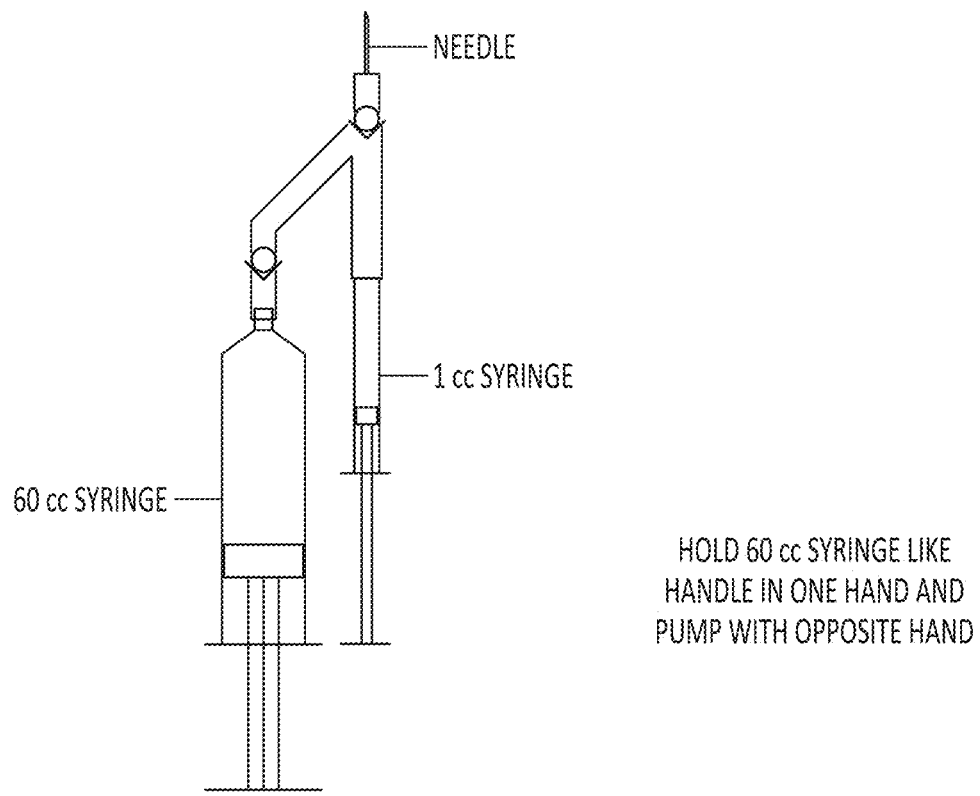
FIG. 16 is an example of an injection apparatus as described herein.

Another embodiment (FIG. 16) would have the user hold the large syringe in one hand and operate the smaller syringe with the opposite hand. The fluid flow would be controlled by check valves in the fluid path. Flow from the large syringe into the small syringe, and flow out from the small syringe into the patient would be restricted by the check valves.

Constant Force Single Syringe Assist Device

Figure 17:
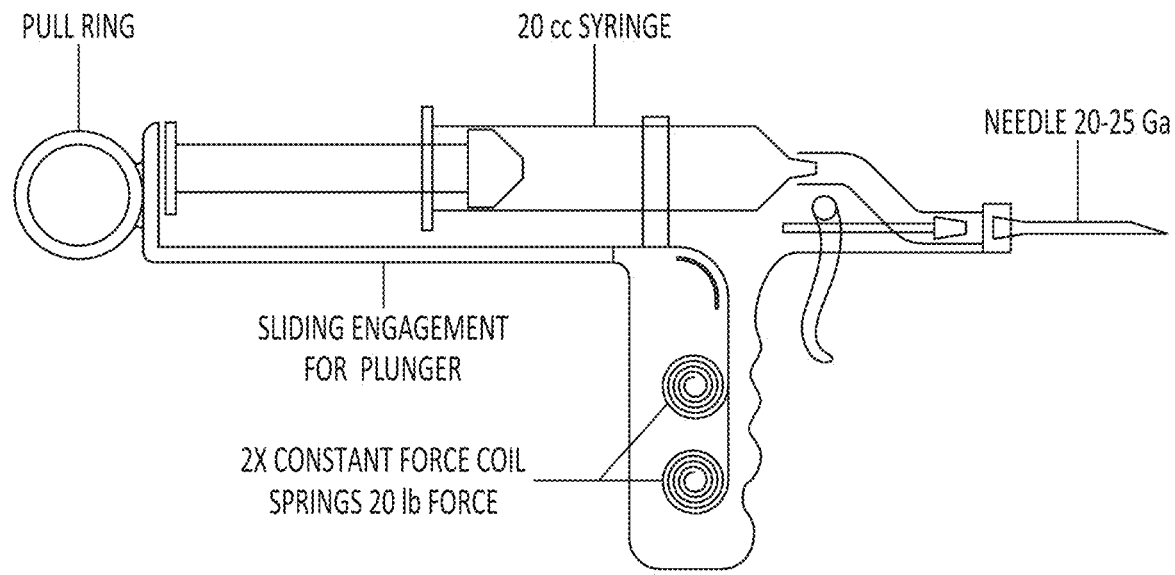
FIG. 17 is an example of an injection apparatus as described herein.

A single syringe may be loaded into a device that applies a constant force to the back of the plunger pushing the fluid out the front fluid passage. See, e.g., FIG. 17. The front passage may have a restrictive mechanism that can close off the flow, have an aspirate function, and an open flow state. The constant force is provided by coil springs contained in the handle of the device. The user will pull back on a pull ring on the back of the device to provide the initial tension in the spring and held by a temporary catch. The filled syringe will then be loaded into the device and secured to the fluid system via a luer lock or similar attachment. The spring mechanism will be engaged with the back of the plunger and the catch is released to apply the force to the plunger. The device is ready for use and the fluid flow is controlled by the user by the front trigger.

Fenestrated Needle for Injection of Anesthetic

Full saturation of the tissue with local anesthetic is desired to achieve maximum effectiveness. The technique is to make multiple injections in the tissue injecting 1-2 cc's at each injection. The user will insert the needle deep into the tissue and inject as they withdraw the needle to saturate that localized area. This is an effective way to deliver the medication. However, when the tip of the needle is in dense tissue or pushed up against a bone the resistance can be very high. When this situation occurs, the user cannot deliver enough pressure to force the fluid out or the fluid may be pushed out the tip and flow up the side of the needle in the whole that was created by the needle without penetrating the tissue.

Figure 18A:
FIGS. 18A-18B show examples of needles that may be used with any of the apparatuses described herein.
Figure 18B:
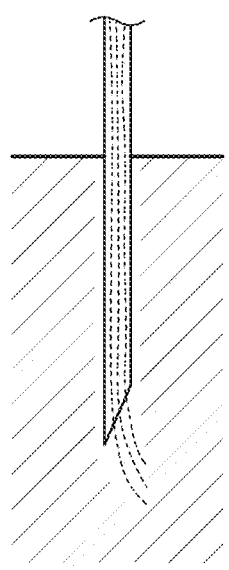
Figure 18B:
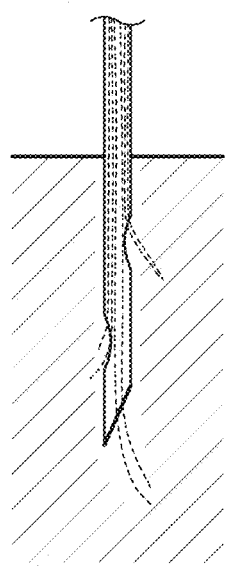
Figure 19A:
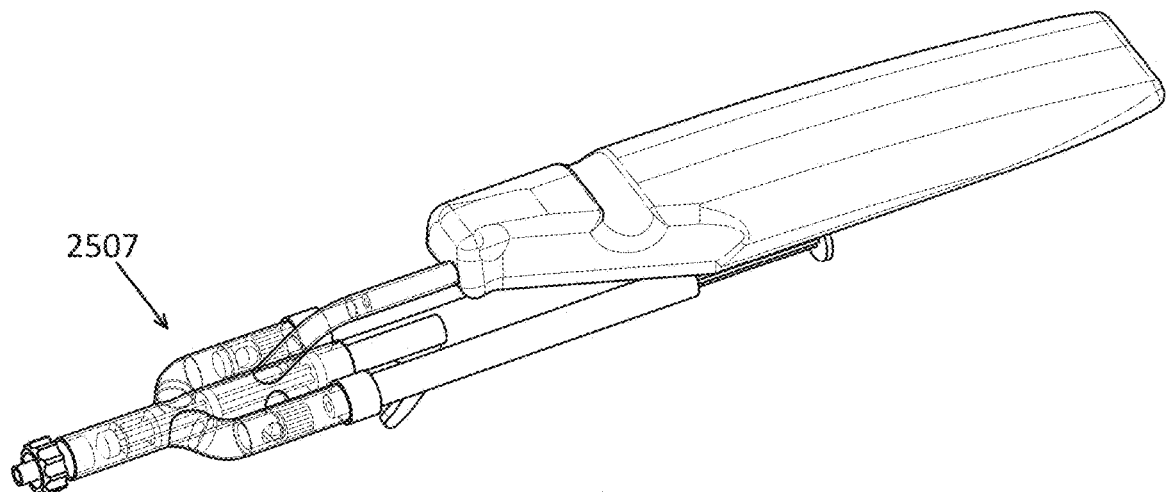
FIGS. 19A-19D is an example of a manifold assembly of an injection apparatus as described herein.
Figure 19B:
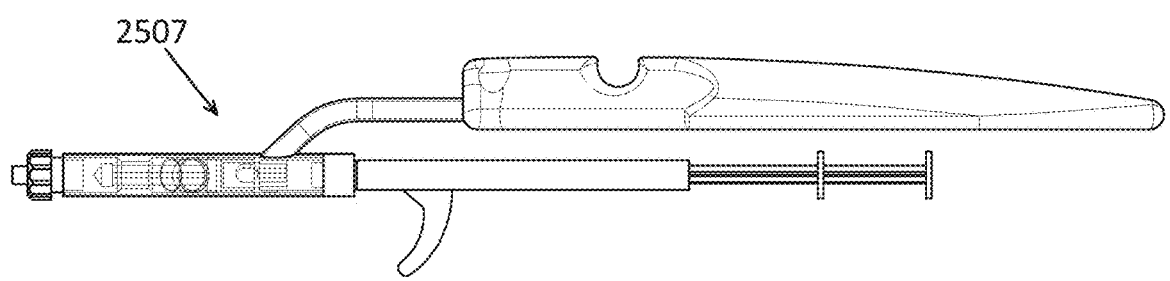
Figure 19C:
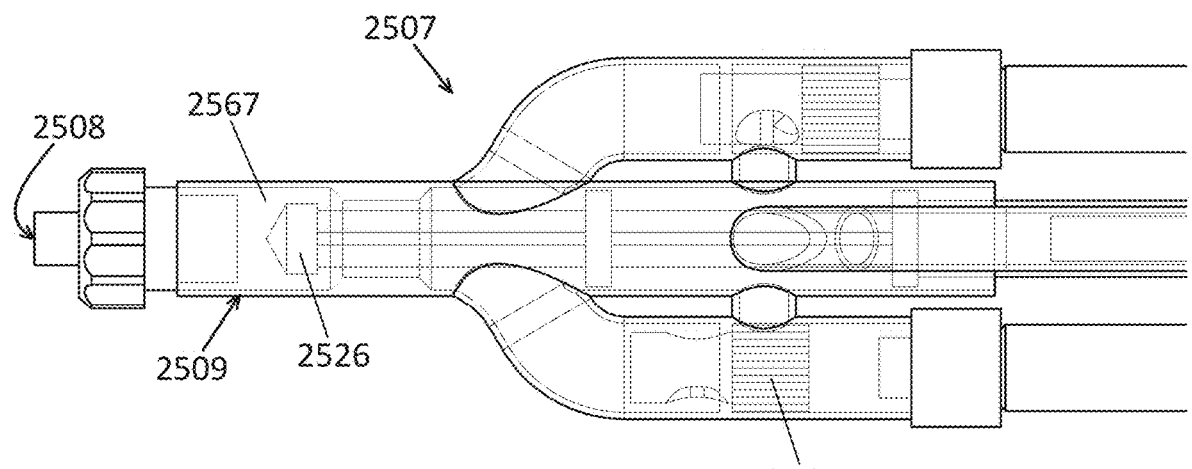
Figure 19D:
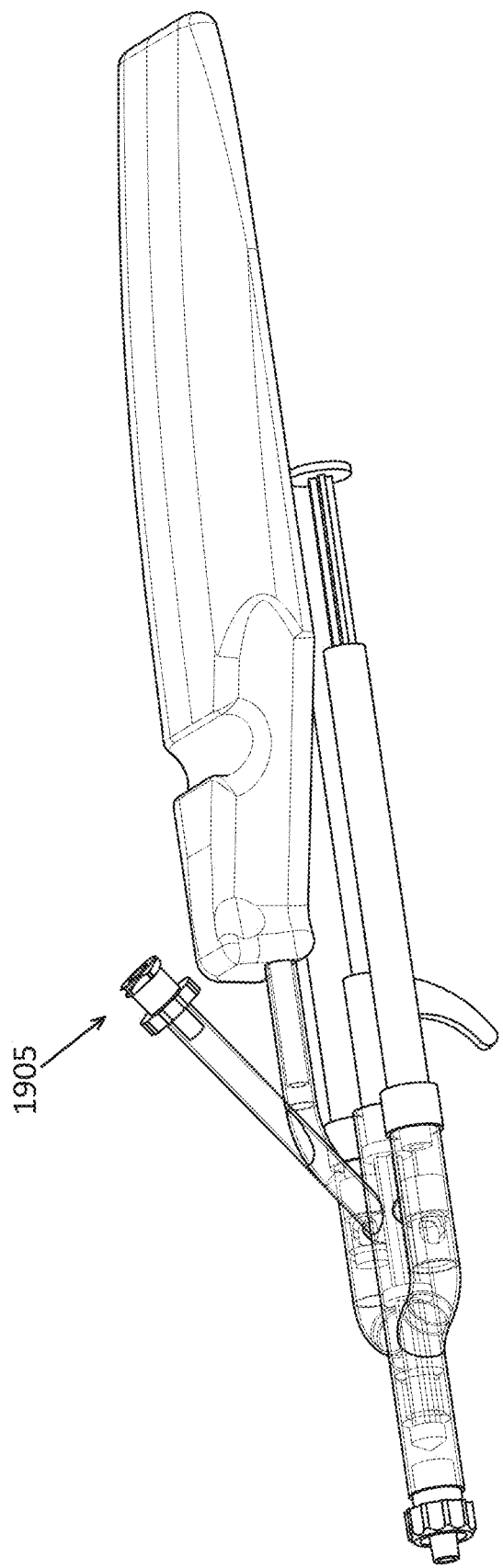

To increase the saturation and reduce the occurrences of high pressure and fluid loss due to dense tissue, a needle with side ports in addition to the end port is used for injections. When this is used the user will insert the needle and push fluid into the site. The fluid will flow out the tip and the side ports more effectively saturating the tissue. If any of the ports is in dense tissue, then there are other open ports for the fluid to flow and saturate the tissue. See, e.g., FIGS. 18A-18B.

Systems for Injecting Materials

Also described herein are systems and methods for injecting fluids having a manifold that includes a selection channel and a function selection piston in the selection channel that is configured to move within the selection channel, and an actuation control configured to drive the function selection piston within the selection channel so that, at a start of an actuation of the actuation control, the function selection piston causes aspiration into the selection channel from the delivery port, further wherein continuing the actuation of the actuation control moves the function selection piston so that the first piston chamber and the second piston chamber are in fluid communication with the delivery port, so that fluid is pumped out of the delivery port from the first piston chamber and the second piston chamber. These methods and apparatuses may improve upon and modify the apparatuses (including manifolds) described of U.S. Pat. App. Ser. No. 17/223,976, now U.S. Pat. No. 11,229,750, (and in corresponding PCTUS2021025868). As mentioned, in some examples this manifold may include a function selection piston or plunger; the function selection piston may incorporate both aspiration and pumping and may move in a single direction to achieve from out of the same delivery port. In general, any of the features described in any of the figures and text above may be incorporated into any of the other features.

Figure 13:
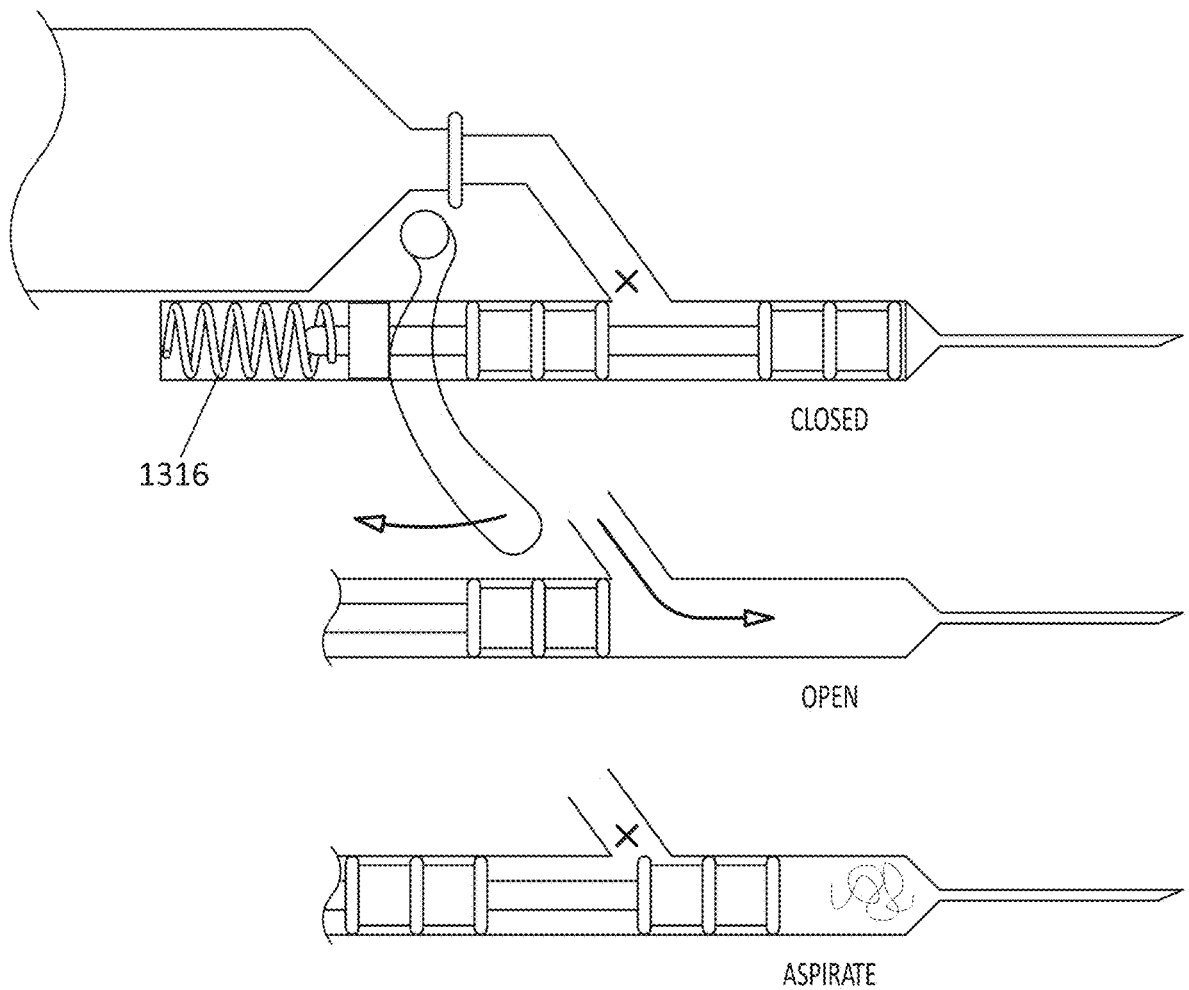
FIG. 13 is an example of a manifold of an injection apparatus as described.
Figure 20:
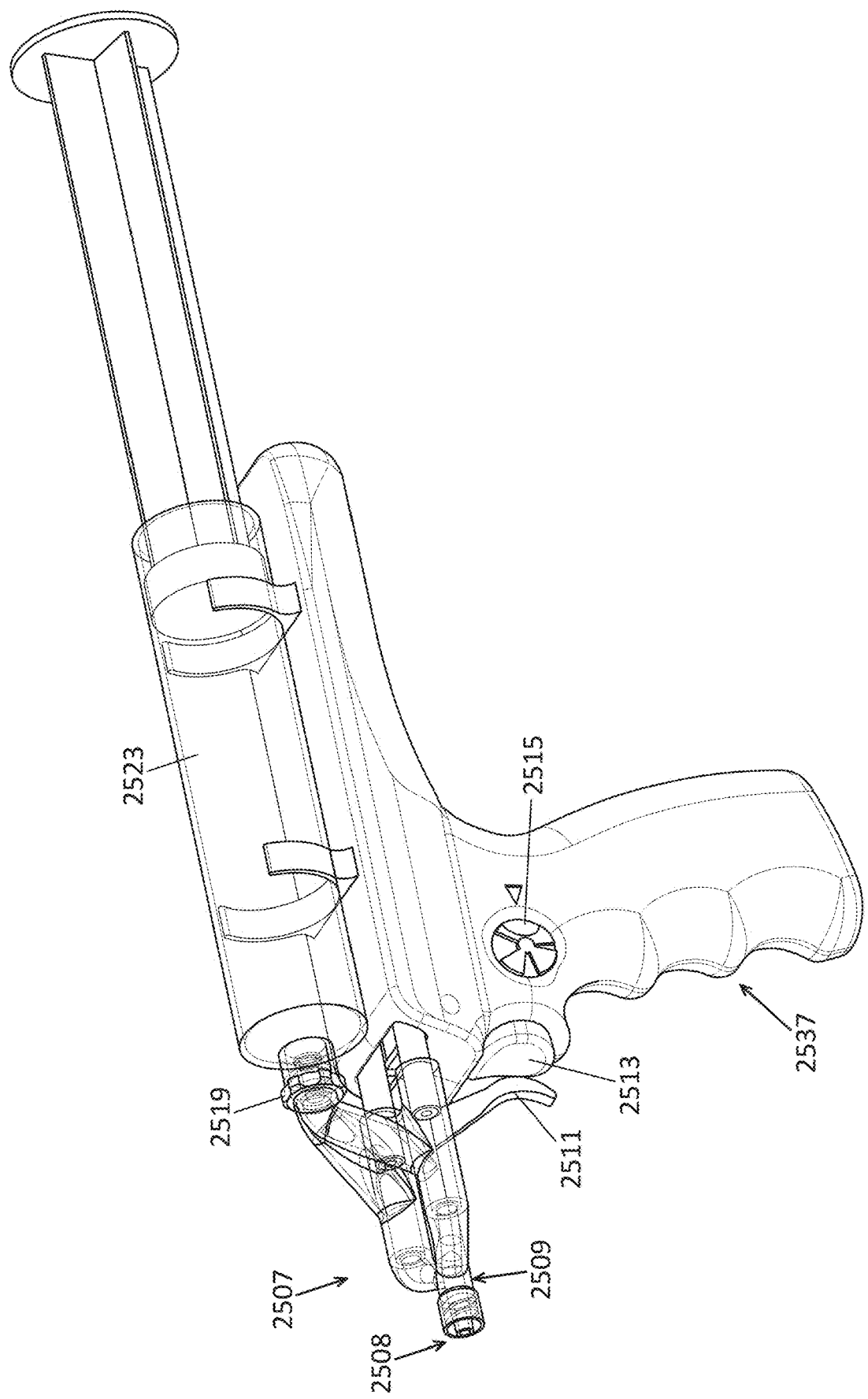
FIG. 20 is an example of an injection apparatus as described herein.
Figure 21A:
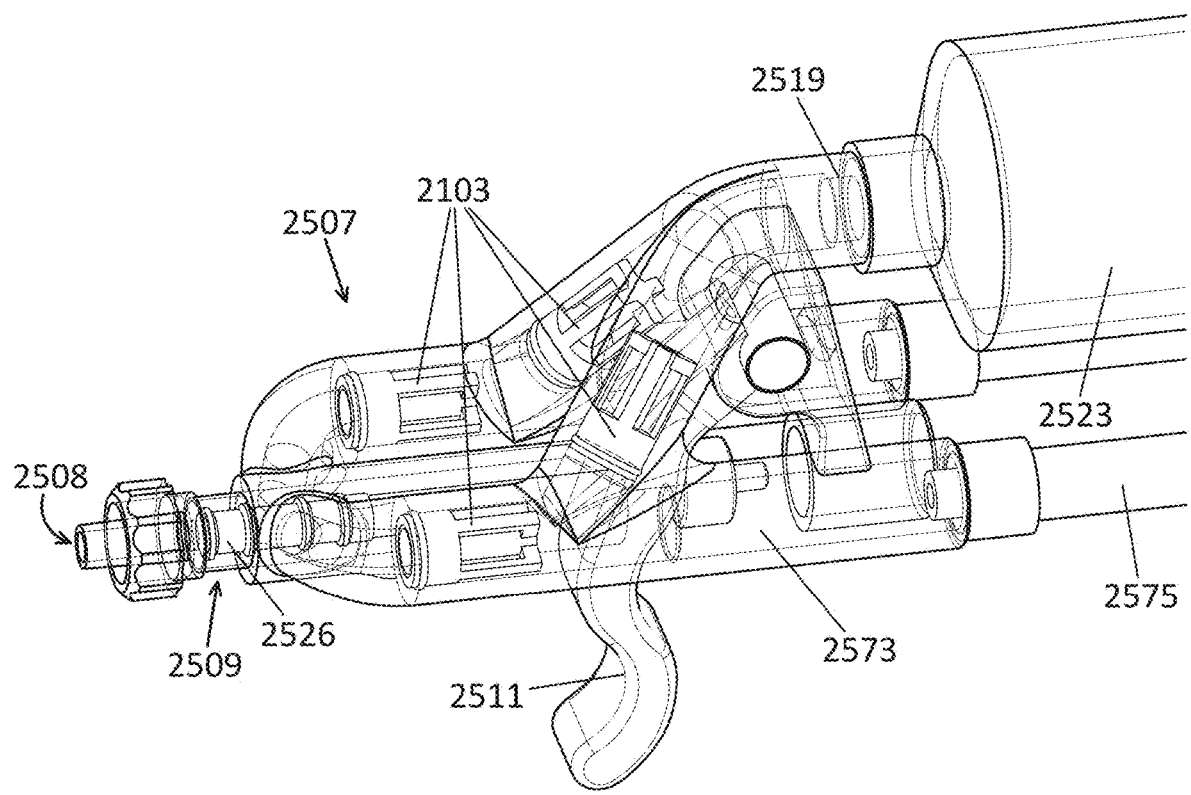
FIGS. 21A-21C illustrate an example of a manifold assembly of an injection apparatus as described herein.
Figure 21B:
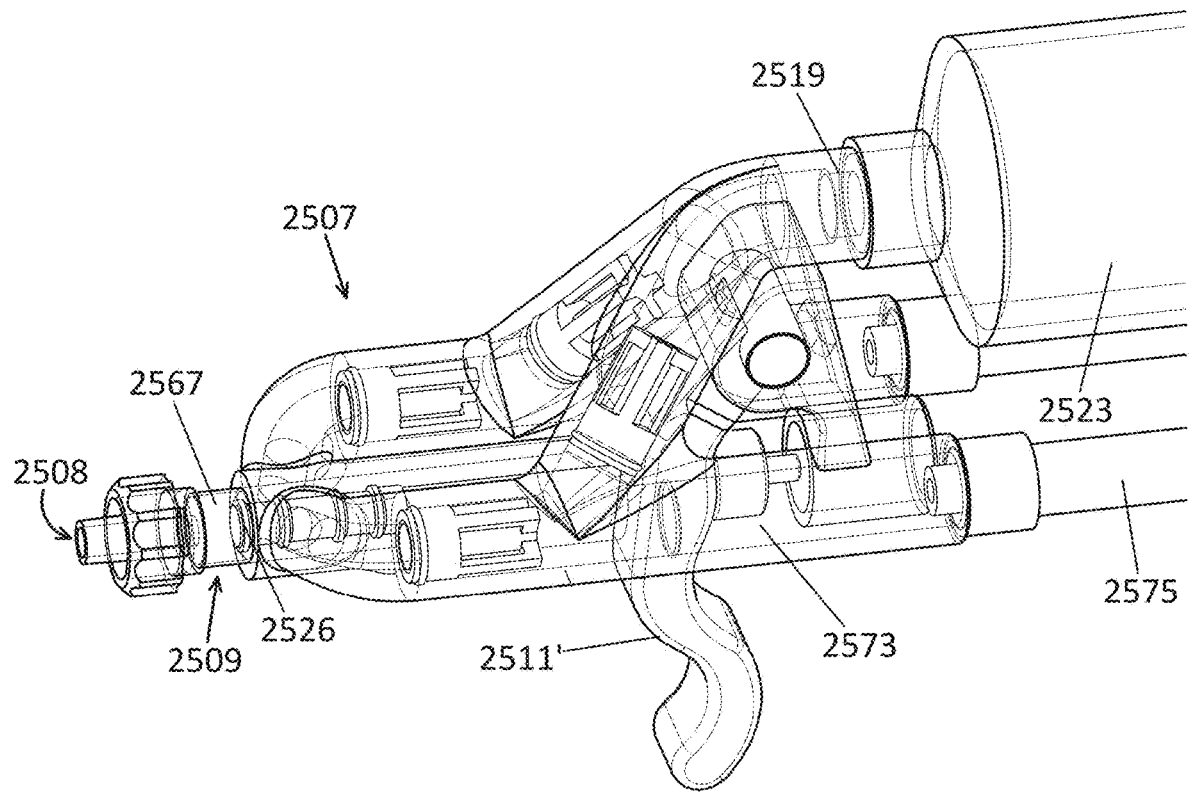
Figure 21C:
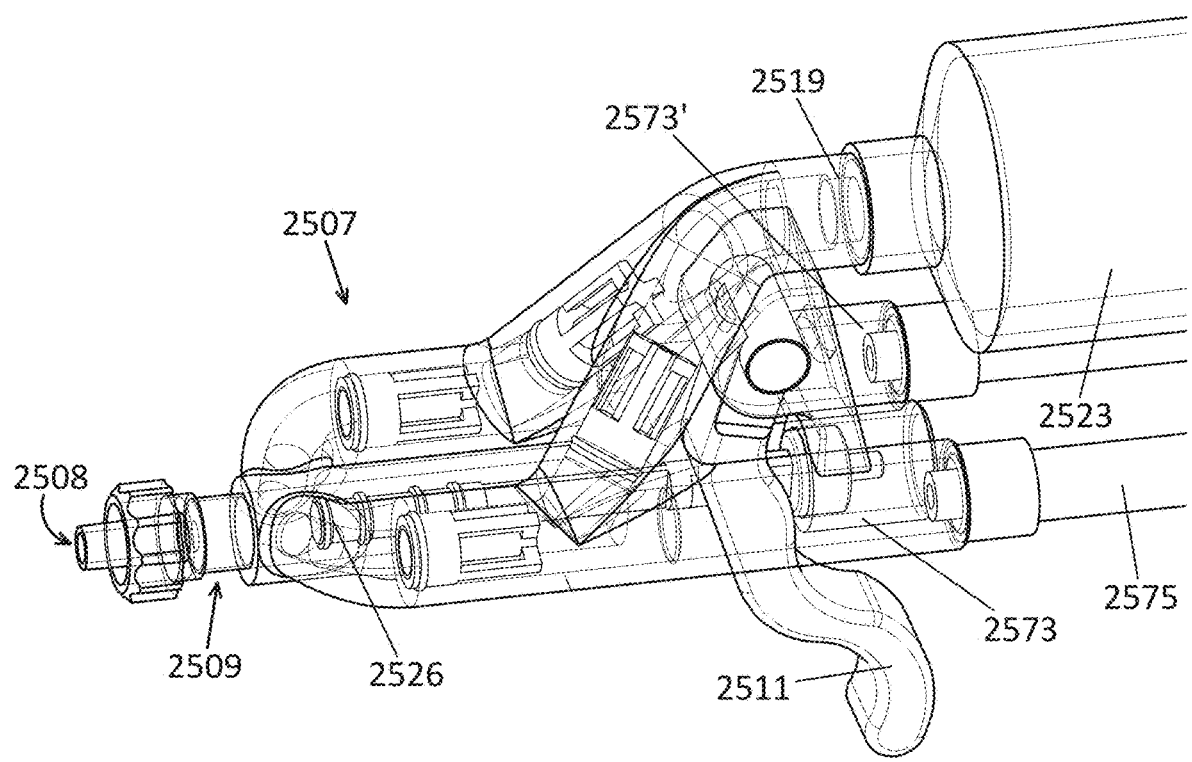

For example, FIG. 20 illustrates an apparatus including a manifold 2507 as described herein (reference is also made to FIG. 13, showing a side view of a manifold region including a return bias 1316). In this example, the smaller syringes on the sides (e.g., 1 cc syringes) may be loaded from the larger (e.g., 25 cc, 10 cc, etc.) syringe on the top. The smaller syringes may be referred to as a first piston chamber 2575 and second piston chamber. FIGS. 21A-21C illustrate operation of one example of this manifold assembly 2507. In FIG. 21A, the fluid path is fully closed, and the motor is off (e.g., when the control, e.g., trigger 2511, is fully released). In FIG. 21B, the apparatus may aspirate when trigger 2511' is pulled (e.g., −2 mm); alternatively, in some examples aspiration maybe triggered with the trigger is pushed forwards, and the device configured accordingly. Aspiration material (e.g., from within a body) is pulled back into the delivery port 2508 into the selection channel 2567 within which the selection function selection piston 2526 may move; pulling the trigger causes the function selection piston to move proximally from the distal end of the selection channel, so that aspiration material is drawn into the aspiration chamber (e.g., the distal part of the selection channel including an aspiration window 2509) in front of the plunger. The fluid path(s) to the 1 cc syringes are still closed and the motor is off.

In FIG. 21C, fluid from the first 2575 and second 2575' piston chambers (loaded from the reservoir 2523 may be pumped when the trigger is fully pulled back. The fluid path may be opened, and motor may be activated by the control (e.g., trigger) 2511.

In this example, the trigger controls a central plunger or function selection piston (see, e.g., FIG. 13). Initially the function selection piston (shown as a double headed plunger in this example) may be fully advanced, so that the distal head occludes the needle output from any input/output. The plunger may be withdrawn proximally, to aspirate material from the needle into the space in front of the withdrawn plunger (e.g., the aspiration chamber) of the selection channel 2567. This region may include an aspiration window 2509. Further withdrawing the plunger (by further actuating the control, e.g., trigger) couples the two 1 cc injection chambers in fluid communication with the delivery port 2508 and with a needle that may be coupled to the delivery port, as shown in FIG. 21C.

The embodiment shown in FIGS. 20-21C includes four one-way valves 2103 (e.g., first check valve 2103, second check valve 2103', third check valve 2103", and fourth check valve 2103'''), preventing from the 1 cc injection chambers back into the refilling (larger volume) chambers and preventing flow (e.g., aspirate) form entering either the smaller (e.g., 1 cc) injection chambers or the refilling chamber.

Other refilling reservoirs may be used. For example, FIGS. 19A-19D show another example of a manifold 2507 similar to that shown in FIGS. 20 and 21A-21C. The variation shown in FIG. 19D also includes an optional fill port on top 1905. This variation may include an inline check valve and could be filled when the trigger is pulled back into the aspirate position.

In general, these apparatuses may include a drive assembly including a belt drive to drive alternating injection by the reciprocating smaller-volume (e.g., 1 cc) syringes. The belt drive may be able to create enough speed and torque to achieve at minimum, e.g., 1 cc, 2 cc, 3 cc, 4 cc, etc. of fluid injected per second. Some variations may have a minimum of 4 cc per second.

Flow through the manifold may be driven by the motor of the drive assembly; the motor may be driven fast enough to do two full cycles per second (or faster). In some examples the small injection chambers may be 2 cc syringes. Other flow rates (e.g., 2 cc/second or faster) may be used. For example, flow may be approximately 15 seconds of flow for a 60 cc tank; is some examples, 30 seconds for a 60 cc tank, etc.

The drive assembly may be part of a handle portion that is configured to couple and engage with a separate fluid-handling portion, as described below. Any of the apparatuses described herein may be configured so that the motor drives a drive belt in one direction only, rather than reciprocating the drive belt; alternatively in some examples the apparatus may be configured so that it be toggled between driving in one direction and driving in multiple directions (e.g., switching between the two). For example, the apparatus may be used to deliver particularly viscus or small dose materials, such as Heron's Zynrelf (Bupivacaine/meloxicam). Zynrelef is a viscous material (e.g., having a viscosity akin to that of honey) and typically only a small volume is administered (e.g., 14 ml or less). In some examples the apparatus may include a control (e.g., switch) to toggle between the drive belt reciprocating (e.g., going back and forth) and driving in just one direction. In general, the apparatuses described herein may be adapted to minimize the flow path length when delivering highly viscus materials.

Any of the apparatuses described herein may also or alternatively be configured to regulate the temperature of the material to be injected. The apparatus may include one or more regions of control for controlling the temperature of the material within the apparatus. In some examples, the apparatus may heat or warm the fluid to be delivered to any temperature (e.g., between 20 degrees C. and 100 degrees C.). The apparatus may include control circuitry to control the temperature of the reservoir and/or piston regions. The apparatus may include insulative material to prevent heating the user's hand when operating the apparatus. The control circuitry may include one or more sensors (e.g., thermistor) to regulate the temperature with a range. The temperature range may set (preset) or may be manually and/or automatically selected. In any of these apparatuses the apparatus may include one or more circuits that connect heating coils to the battery or power supply/power regulator. In some examples of apparatuses including a separate upper (e.g., disposable) and lower (reusable) components, when the upper (typically fluid half) is mated to the lower half of the apparatus, the circuit may be activated, and the apparatus may warm the fluid. For example, by applying heat to warm the fluid path in the upper half. In some examples the apparatus includes heating components, such as heating coils that may be adjacent to the reservoir to warm the medication to be administered.

Figure 23:
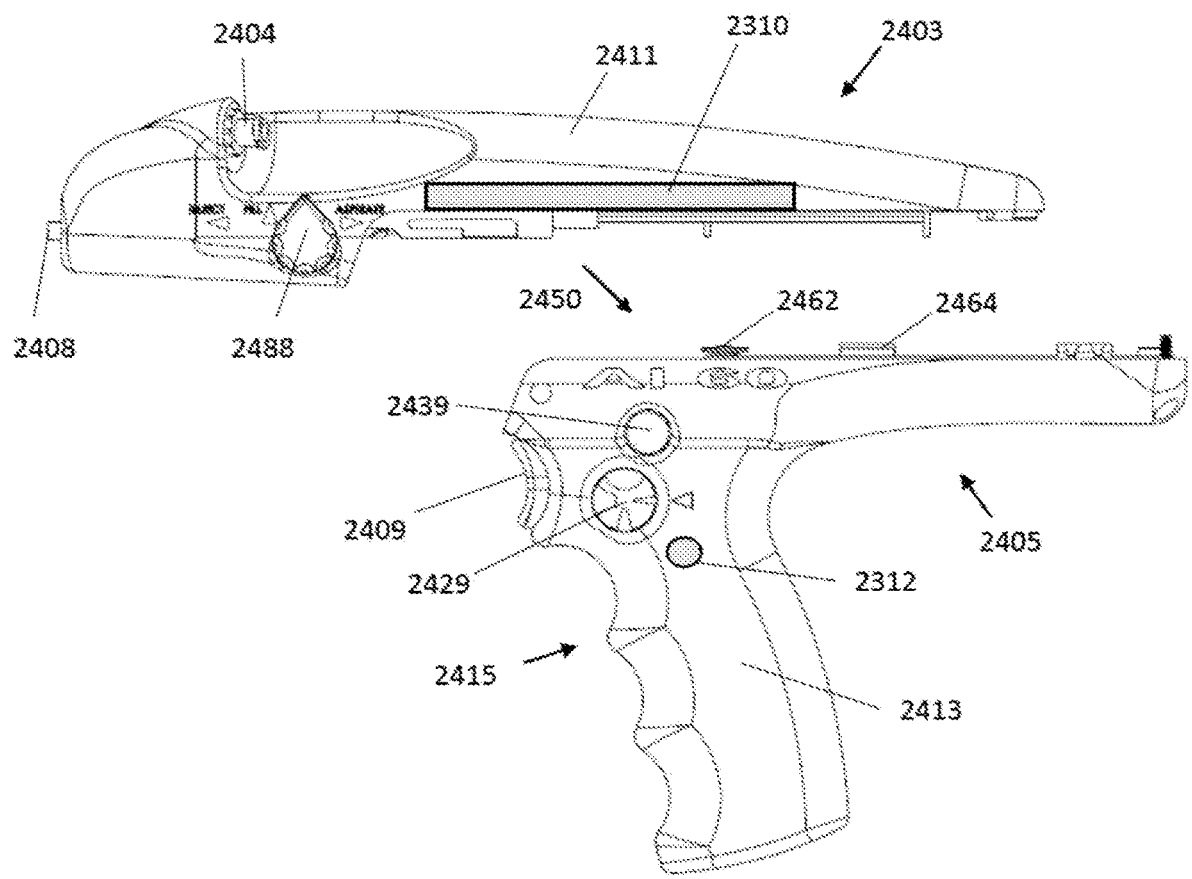
FIG. 23 illustrates an example of an apparatus as described herein.

For example, FIG. 23 illustrates an example of an injection apparatuses (device, system, etc.) as described herein configured as two or more component devices that may be combined prior to use. Either or both may include the heating components. The apparatus may optionally include a control as mentioned above for switching between one-directional movement of the drive belt and alternating movement. For example, FIG. 23 illustrate an example of a two-component (two-part) apparatus having an upper, fluid-handling portion 2403 and a lower handle portion 2405. In this example, the fluid-handling portion includes the portions that contact and direct fluid in the device. For example the first (upper) housing 2411 of the fluid-handling portion may enclose a reservoir, and a first and second piston chamber, as well as a manifold including the plurality of check valves (not visible in FIGS. 24A-24B). The fluid-handling portion also includes a delivery port 2408 and a fill port 2404. In addition, the fluid-handling portion also drive assembly including a transmission that is operatively connected to a first piston in the first piston chamber and a second piston in the second piston chamber so that the drive assembly can reciprocally move the first and second pistons. The apparatus may include a control (e.g., switch 2312) for toggling between reciprocating movement and one-directional movement of the drive belt.

In FIG. 23, the fluid-handling portion also includes a selector control 2488 that includes three positions (inject, fill, and aspirate), shown marked on the housing. The fluid-handling portion may be coupled 2450 to the lower, handle portion 2405. The handle portion may include a second housing 2413 that includes a grip region 2415. The handle portion may also include one or more controls for operating the device, such as a trigger control 2409 and a fluid volume control 2429. In this example, the fluid volume control is configured as a dial that may be rotated to select between three fixed-volume settings a continuous flow setting (e.g., 1 cc, 2 cc, 3 cc and continuous). The handle portion may enclose or partially enclose the driver (e.g., motor) and control circuitry (e.g., controller). The handle portion (or in some examples, the fluid-handling portion) may include one or more indicators, such as an indicator light (e.g., LED) 2439 that may indicate, for example, power status (on/off, etc.), error (over-pressure, empty reservoir, etc.), in use/ready, etc.

The apparatus may also include one or more heaters 2310, such as thermoelectric heaters, resistive heaters (coils, plates, etc.). The one or more heaters may be controlled by a controller, e.g., in the handle portion 2413 and/or may include input from one or more sensors (e.g., temperature sensors). The controller may receive input from the sensors and/or input to set the temperature. Thus, the handle may include a selector for selecting the temperature and/or for turning heating on/off. As mentioned above, the apparatus may include an insulating material to thermally insulate the heating components and heated fluid from the rest of the apparatus and/or the user.

The fluid-handling portion and the handle portion may be combined together by engaging one or more coupling features 2464 on the fluid-handling portion and/or the handle portion. In particular, the driver in the handle portion may engage 2462 with the drive assembly (including the transmission operatively connected to the pistons of the piston chambers) so that the driver may controllably drive fluid out of the injection port of the device. Thus, in some examples the apparatus may include an upper fluid subassembly (fluid-handling portion) and a lower handle portion. This configuration may allow different sterilization methods for each portion, such as gamma sterilization for the fluid-handling portion and ethylene oxide gas sterilization for the handle portion (containing electronics that may be sensitive to some sterilization techniques).

The multiple parts (the fluid-handling portion and the handle portion) of the apparatus may be packaged separately, in sterile packaging, and may be combined prior to use. In some examples combining the two parts may activate the device (e.g., turn it "on") and separating the two parts may de-activate the device (e.g., turn it "off") so that a separate "on" switch is not needed. In some variations a separate "on/off" switch may be included. In some examples the fluid-handling portion may be disposable, single-patient use and the handle portion may be re-usable with multiple fluid-handling portions (including with multiple patients). Thus the handle portion may include rechargeable batteries and may be re-charged during use. In some examples a separate "battery" portion may be swapped into the handle portion, allowing already-charged batteries to be swapped into the handle (e.g., the apparatus may include three components, rather than just two). Any of the apparatuses described herein may be used with a cord that may provide power from a wall source (e.g., plug or plug and adapter).

The controller may be configured to operate autonomously, or it may be configured to communicate, e.g., wireless (via Wi-Fi, Bluetooth, etc.) to a remote server. In some examples the apparatus may transmit status information to a remote server and/or to a handheld device (e.g., phone, etc.). For example, the apparatus may transmit cycle counts, power status, fill status, error status, temperature, etc. Alternatively or additionally the apparatus may include a display on the device (e.g., on the handle portion) for displaying any of this information.

In some examples the fluid-handling portion may be locked (including releasably locked) to the handle portion. The lock may be a latch (e.g., including a hook, snap, clasp, etc.) and may include a release on either or both of the fluid-handling portion and/or the handle portion. In some examples the lock may be on the housing (shell) portion or may be coupled to the housing(s), such as the housing for the fluid-handling portion and the housing for the handle portion. The lock may prevent separation of the handle portion and the fluid-handling portion unless and until the lock is disengaged.

As mentioned, the handle portion may include the controller or control circuitry. In some examples the apparatus includes firmware that may incorporate a calibration function (e.g., performed at the factory) where pressure and vacuum are alternately cycled, and sensor values tabulated. The firmware may linearize the data and store permanent coefficients in EEPROM memory to use for monitoring routines when the apparatus is operating. The calibration process may reduce the need for precision assembly and tight tolerances.

The pressure-sending subassembly within the apparatus may allow the processor to detect when pressure exceeds a safe threshold and it may alert the user and/or protect the apparatus, e.g., by disabling the driver and/or venting the device. Additionally, if the device is being operated with and empty reservoir, vacuum may be detected, and the device may issue an alert and/or disable the driver.

Figure 24:
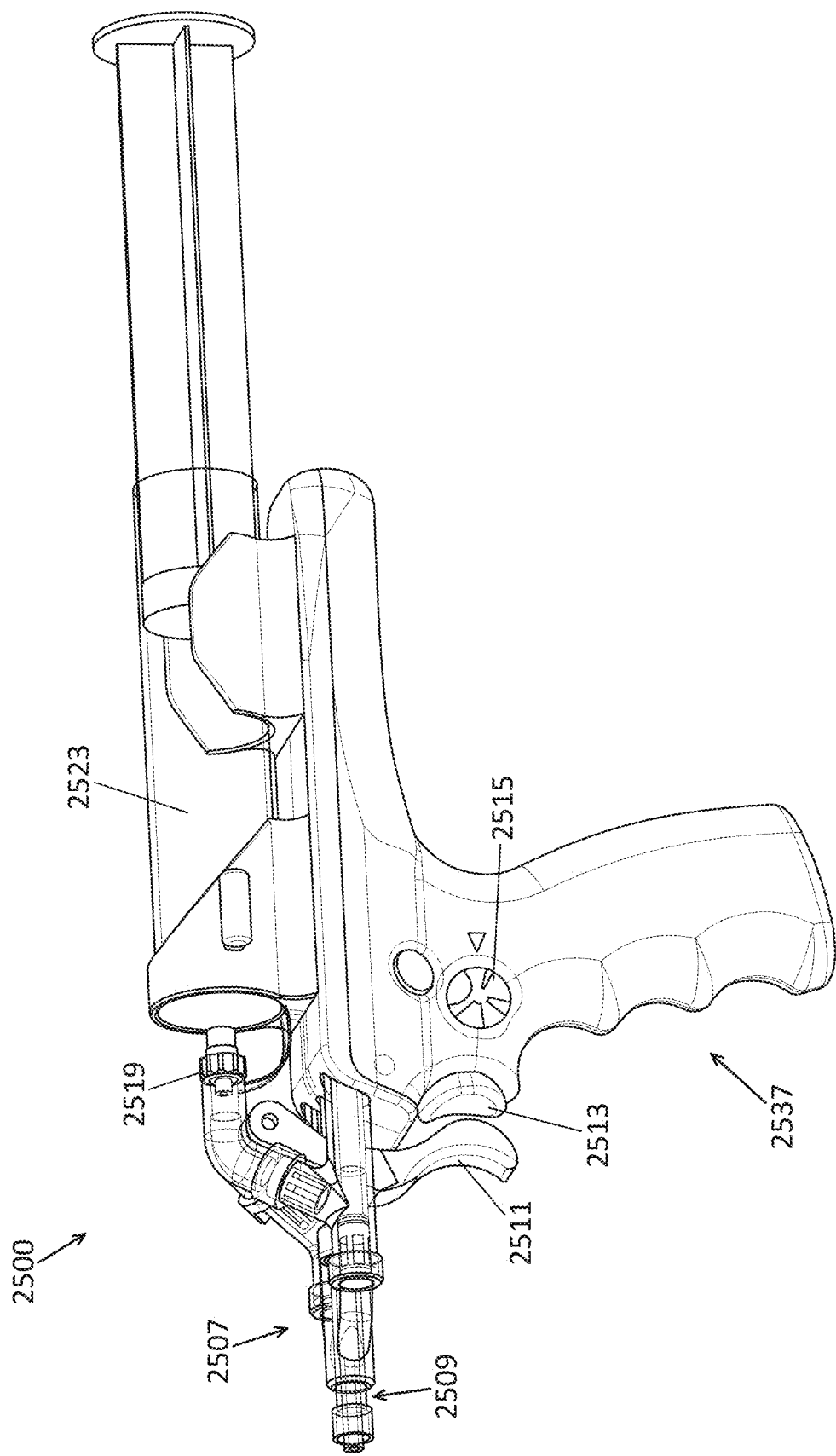
FIG. 24 is an example of a hand-held injection apparatus as described herein.

FIGS. 24, 25A-25C, 26A-26B and 27A-27B illustrate another example of a system for injecting a material similar to those shown and described in FIGS. 20 and 21A-21C. FIG. 24 shows an overview of the apparatus, configured as a hand-held injector system 2500, that includes a lower handle portion including a grip 2537 and a housing enclosing the drive system (not visible in FIG. 24) and control circuitry. In FIG. 24 the handle portion also includes an optional dose selector 2515 and a pump control (e.g., pump on/off). In some examples the pump control may be integrated into or with the actuation control (e.g., trigger) 2511. In this example, the actuation control is configured to engage with the separate pump control at an appropriate point during actuation of the device, as will be described in greater detail below.

Figure 26A:
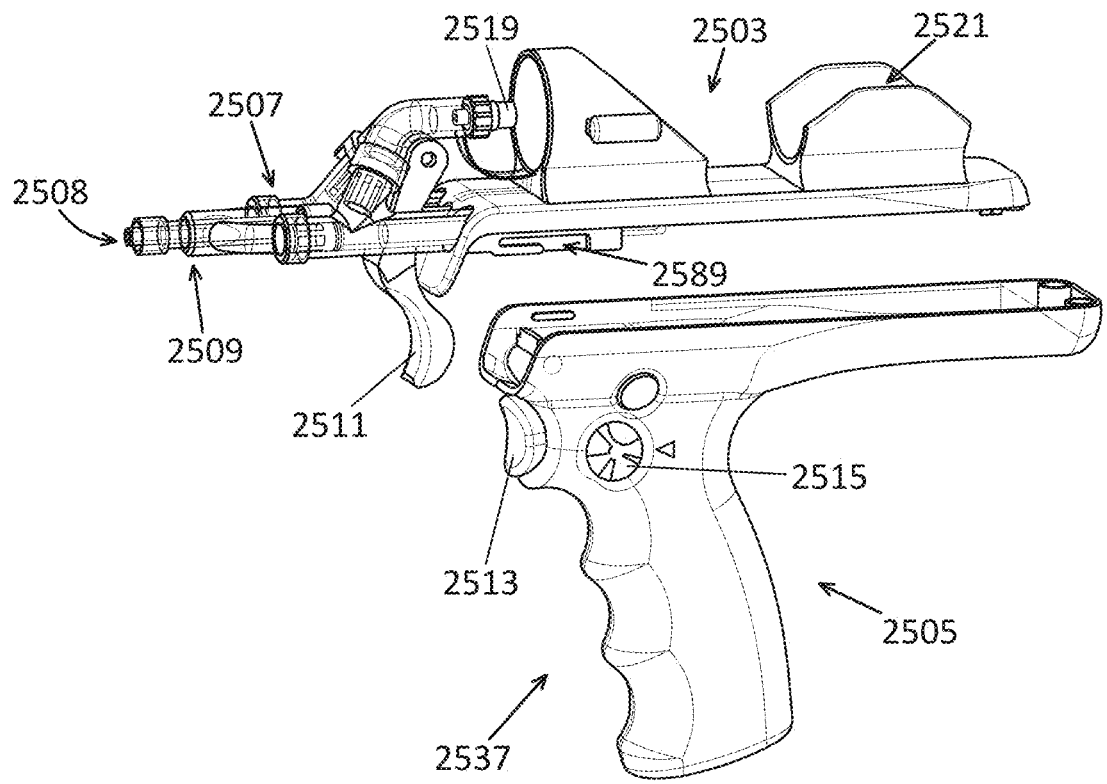
FIGS. 26A and 26B illustrate the assembly of the upper fluid-contacting portion with the fluid-handling portion and a handle portion to form the hand-held injection apparatus.
Figure 26B:
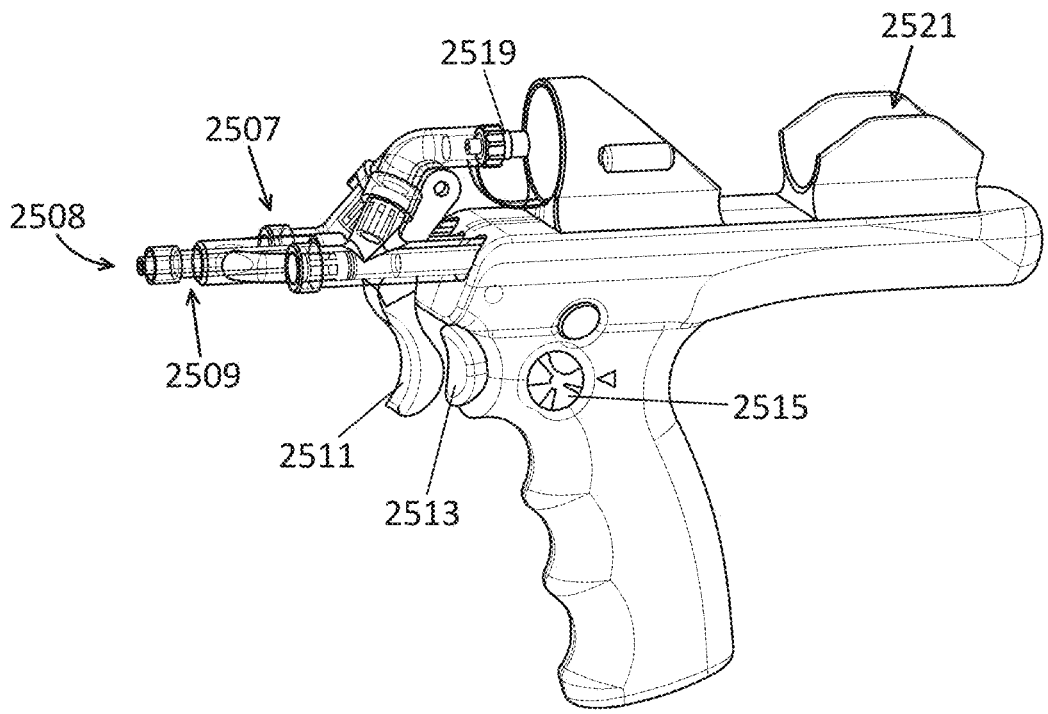

The handle portion may be fully engaged with an upper fluid-handling portion, as will be described in reference to FIG. 26A-26B, below. The upper fluid-handling portion may include the manifold 2507 which may itself include a selection channel extending proximally to distally, and a function selection piston 2526. A delivery port 2508 is at the distal end and in fluid communication with the selection channel 2567 portion of the manifold. The manifold may also include a first piston channel 2573 fluidly coupled to the first piston chamber and a second piston channel 2573' fluidly coupled to the second piston chamber, similar to the configuration shown in FIGS. 21A-21C. The first piston chamber is fluidically connected to the selection channel through the first piston chamber and is also fluidically connected to the reservoir port 2519. A reservoir 2523 may be coupled to the reservoir port (e.g., via a lure lock). One-way valves (e.g., check valves) 2103, 2103' may be positioned within the manifold to regulate the flow of fluid from the reservoir port into the first and second piston chambers to allow refilling of the piston chambers without permitting back flow from the piston chambers back into the reservoir. One-way (e.g., check) valves 2103 may also be positioned between the selection channel of the manifold and the first and second piston chamber (e.g., via the piston channels) to permit fluid to be ejected into the selection channel and out of the delivery port when reciprocating the pistons of the first and second piston chambers but preventing back flow from the selection channel back to first or second piston chambers.

Figure 25A:
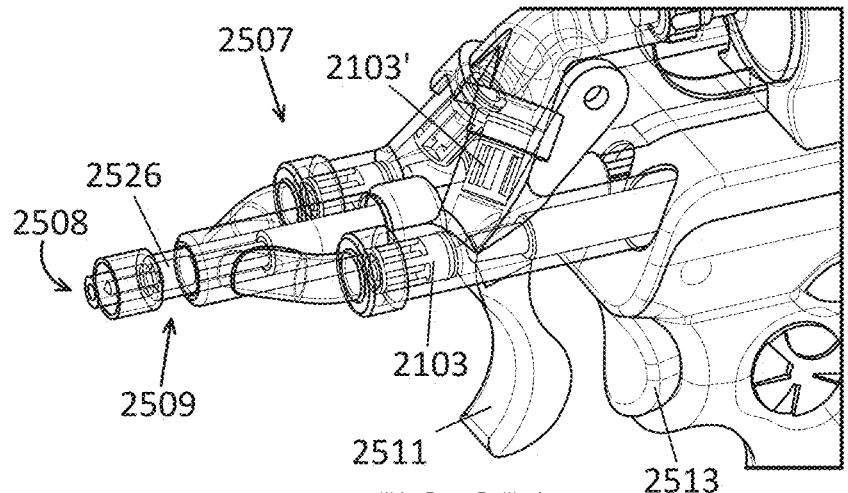
FIGS. 25A-25C illustrate operation of a manifold of a hand-held injection apparatus.
Figure 25B:
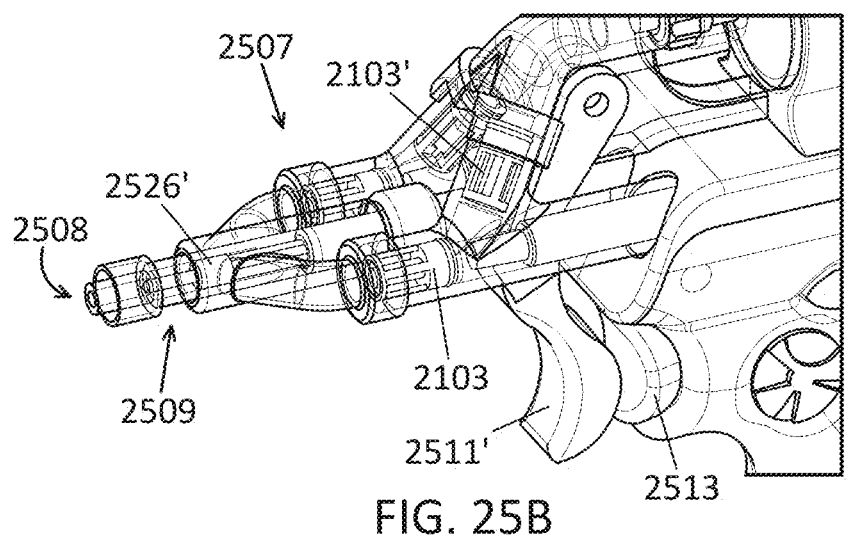
Figure 25C:
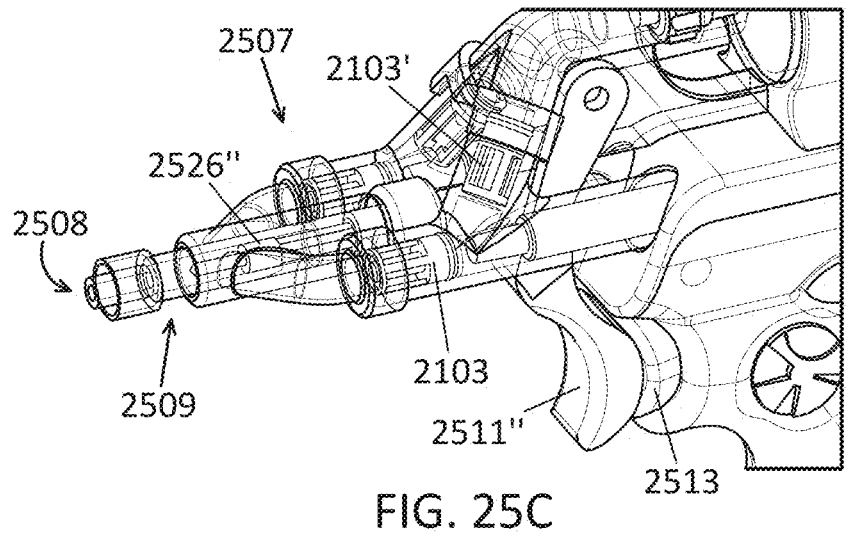

FIGS. 25A-25C illustrate operation of the apparatus of FIG. 24, and in particular, the operation of the function selection piston. In general, the apparatus may be operated by operating the actuation control 2511. In FIG. 24 and FIGS. 25A-25C the actuation control is a trigger, but other configurations (buttons, sliders, etc.) may be used. The actuation control is coupled to the function selection piston 2526 within the selection channel of the manifold 2507. The piston includes a piston head (or heads) that is shown extended fully distally in FIG. 25A so that it abuts and blocks the delivery port 2508 at the distal end of the apparatus. The selection channel extended distally to proximally and is in fluid communication with the delivery port. In FIG. 25A the function selection piston and the actuation control (trigger) are in the rest (unactuated) confirmation. In some examples a bias (e.g., a return bias, not shown in FIG. 25A, but similar to that shown in FIG. 13) may be coupled to the actuation control and/or the function selection piston applying a bias force to drive the function selection piston distally.

In FIG. 25B the actuation control (e.g., trigger) 2511' has been actuated (pushing proximally in this example), moving the function selection piston 2526' proximally so that it aspirates out of the delivery port 2508, pulling aspiration material into the selection channel, and in particular into the distal end region ("aspiration region") of the selection channel, which includes an aspiration window 2509 that is at least partially transparent, to allow visualization of blood, for example. In both FIGS. 25A and 25B the fluid connection between the first piston chamber and the selection channel is blocked by the function selection piston, as is the fluid connection between the second piston chamber and the selection channel.

In FIG. 25C the actuation control (e.g., trigger) 2511" has been further actuated, e.g., continuing to push it proximally, driving the function selection piston 2526" even further proximally, so that the head(s) of the function selection piston no longer occlude the connection between the selection channel and the first or second piston chambers (e.g., through the first and second piston channels). The actuation of the actuation control (trigger 2511") beyond this position also actuates the drive, reciprocating the first and second pistons in the respective first and second piston chambers to drive fluid from the first or second piston chambers into the selection channel and out of the needle connected to the delivery port 2508.

In the example shown in FIGS. 24 and 25A-25C, the actuation control 2511, 2511', 2511" engages with a second control (pump control 2513) as it is actuated, to turn on the reciprocation of the first and second pistons. In some examples this second control (e.g., pump control) may instead be integrated into the actuation control.

In operation, the hand-held injector apparatus (e.g., system) may be used to inject a fluid by actuating the actuation control to drive the function selection piston proximally within the selection channel of the manifold. This initial portion of the actuation may apply suction from the selection channel (and out of a needle coupled to the delivery port), so that material is aspirated into the distal region of the selection channel. As mentioned, the aspirated material may be visible through a transparent window in the manifold (e.g., into the selection channel). Actuation of the actuation control may be continued (with or without pause to examine the aspirate), to move the function selection piston further proximally within the selection channel. The more proximal position of the function selection piston may therefore allow relatively unobstructed fluid connection between the selection channel and the first piston chamber and the second piston chamber, and therefore with the delivery port through the selection channel. Further, continuing to actuate the actuation control activates the drive assembly to drive reciprocation of a first piston in the first piston chamber and a second piston in the second piston chamber, pumping fluid out of the needle while alternately transferring fluid from a reservoir into the first piston chamber and the second piston chamber. A controller (e.g., in the handle) may control operation of the drive assembly to control the rate (e.g., flow rate) and/or dose of the injected fluid.

As mentioned, in general these apparatuses may be assembled from a disposable (or limited-use) fluid handling portion 2503 and a durable (ore reusable) handle portion 2505. For example, FIGS. 26A-26B illustrate the assembly of a hand-held apparatus. In FIG. 26A the fluid-handling portion includes the manifold 2507, a delivery port 2508 coupled to the manifold, a reservoir port 2519, a reservoir mount 2521 and the actuation control (e.g., trigger) 2511. The liquid handling portion also typically includes and a first piston chamber fluidically connected to the selection channel of the manifold and in fluid communication with a reservoir port and a second piston chamber fluidically connected to the selection channel of the manifold in fluid communication with the reservoir port, as discussed above. The fluid handling portion 2503 may include one or more engagement (e.g., locking) structures 2589 configured to releasably secure the fluid handling portion to the handle portion. Complimentary engagement features may be present on the handle portion 2505, which may also include a housing enclosing the control circuitry (e.g., one or more processors and/or circuitry, etc.), power regulators, power supply (e.g., battery), and the drive assembly.

Figure 27A:
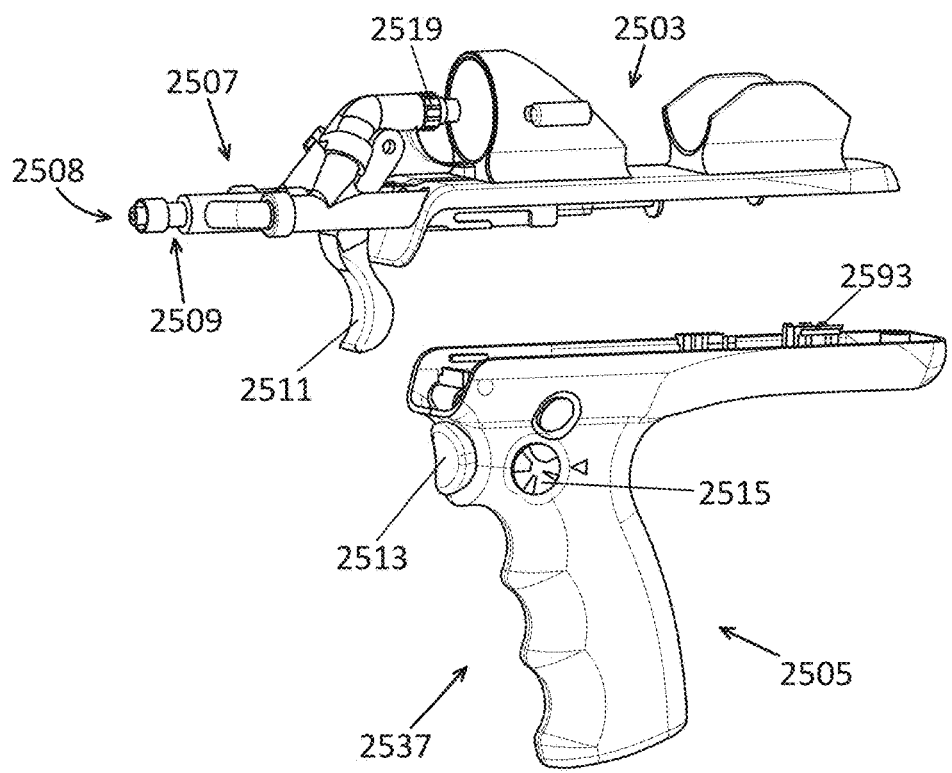
FIGS. 27A and 27B illustrate the mating connection between the upper fluid-contacting portion with the fluid-handling portion in some variations of the apparatuses described herein.
Figure 27B:
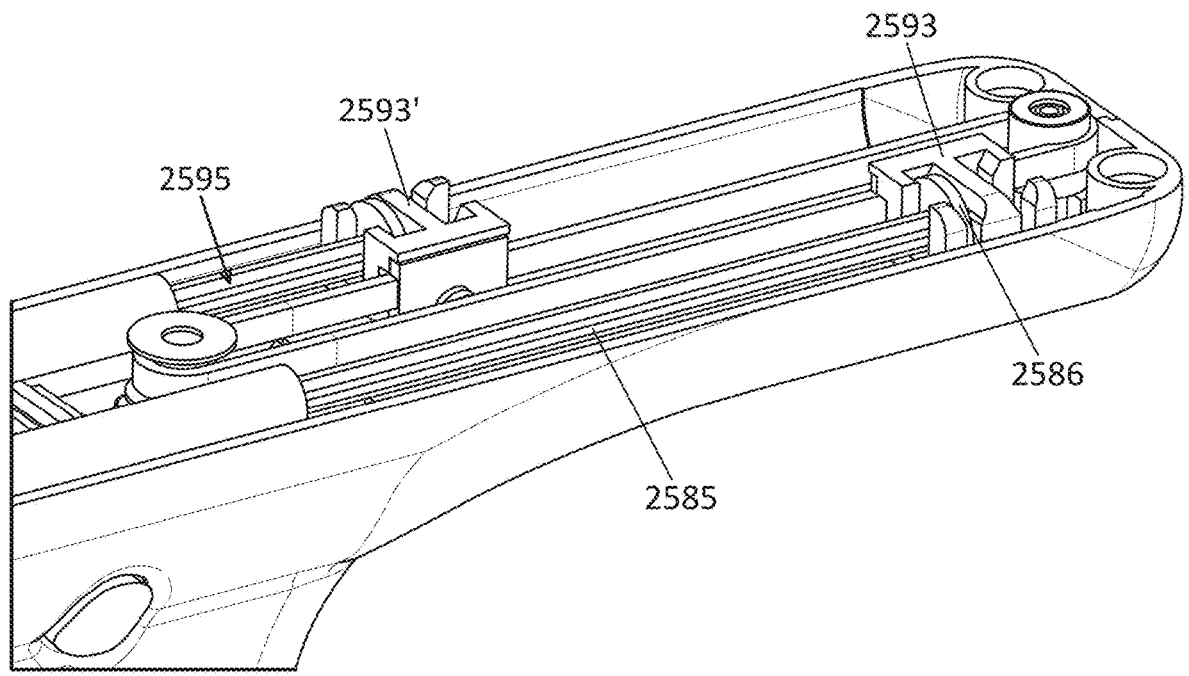

As shown in FIGS. 27A and 27B the drive assembly may be configured to engage with the first 2585 and second 2595 pistons of the first and second piston chambers, respectively. For example, the first and second pistons may engage with a plunger engager 2593, 2593' at a proximal end of the plunger 2586. The plunger engagements may engage with the plungers and reciprocate them to pump fluid as described above.

The fluid handling portion may include a reservoir mount for coupling a reservoir (e.g., a 60 cc syringe) to the apparatus, e.g., via the reservoir port 2519.

It should be appreciated that all combinations of the foregoing concepts and additional concepts discussed in greater detail below (provided such concepts are not mutually inconsistent) are contemplated as being part of the inventive subject matter disclosed herein and may be used to achieve the benefits described herein.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like. For example, any of the methods described herein may be performed, at least in part, by an apparatus including one or more processors having a memory storing a non-transitory computer-readable storage medium storing a set of instructions for the processes(s) of the method.

While various embodiments have been described and/or illustrated herein in the context of fully functional computing systems, one or more of these example embodiments may be distributed as a program product in a variety of forms, regardless of the particular type of computer-readable media used to actually carry out the distribution. The embodiments disclosed herein may also be implemented using software modules that perform certain tasks. These software modules may include script, batch, or other executable files that may be stored on a computer-readable storage medium or in a computing system. In some embodiments, these software modules may configure a computing system to perform one or more of the example embodiments disclosed herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

In general, any of the apparatuses and methods described herein should be understood to be inclusive, but all or a sub-set of the components and/or steps may alternatively be exclusive and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for injecting a fluid, the system comprising:
   a manifold, wherein the manifold comprises a selection channel, a function selection piston that is configured to move within the selection channel, and a plurality of check valves;
   a first piston chamber fluidically connected to the selection channel of the manifold and in fluid communication with a reservoir port;
   a second piston chamber fluidically connected to the selection channel of the manifold in fluid communication with the reservoir port;
   a delivery port fluidically connected to the selection channel of the manifold;
   an aspiration window between the delivery port and the selection channel configured to display aspirated material; and
   a trigger configured to drive the function selection piston within the selection channel so that activating the trigger initially retracts the function selection piston proximally away from the delivery port to aspirate the material into the delivery port, and sustaining the activation of the trigger retracts the function selection piston further proximally in the selection channel to fluidly connect the first piston chamber and the second piston chamber with the delivery port so that the fluid is pumped out of the delivery port from the first piston chamber and the second piston chamber.

2. A method of injecting a fluid using a hand-held injector system that includes a manifold, a first piston chamber, a second piston chamber, and an actuation control, the method comprising:
   actuating the actuation control to drive a function selection piston proximally within a selection channel of the manifold so that material is aspirated into a region of the selection channel having a transparent window from a needle fluidly coupled to the selection channel; and
   continuing to actuate the actuation control to move the function selection piston further proximally within the selection channel to fluidly connect the first piston chamber and the second piston chamber with a delivery port through the selection channel, wherein continuing to actuate the actuation control activates a drive assembly to drive reciprocation of a first piston in the first piston chamber and a second piston in the second piston chamber, pumping the fluid out of the needle while alternately transferring the fluid from a reservoir into the first piston chamber and the second piston chamber.

3. The method of claim 2, further comprising coupling the reservoir to the hand-held injector system.

4. The method of claim 2, further comprising coupling a fluid-handling portion comprising the manifold, the first piston chamber, the second piston chamber, and a trigger to a reusable handle portion including a power supply and the drive assembly to form the hand-held injector system.

5. The method of claim 2, further comprising determining blood was aspirated when actuating a trigger.

6. The method of claim 2, wherein the actuation of the actuation control comprises pulling a trigger.

7. The method of claim 2, further comprising restoring the function selection piston to a distal position after the actuation control is released.

8. The method of claim 2, wherein pumping the fluid out of the needle comprises continuously pumping the fluid out of the needle.

* * * * *